United States Patent [19]
DeFranco et al.

[11] 3,975,399
[45] Aug. 17, 1976

[54] 1,5-DISUBSTITUTED-2-PYRROLIDINONES, -3-PYRROLIN-2-ONES, AND -4-PYRROLIN-2-ONES

[75] Inventors: Robert Jay DeFranco; Richard M. Scribner, both of Wilmington, Del.

[73] Assignee: E. I. Du Pont de Nemours and Company, Wilmington, Del.

[22] Filed: Aug. 6, 1974

[21] Appl. No.: 495,199

[52] U.S. Cl. ................... 260/326.2; 260/326.43; 424/244
[51] Int. Cl.² ............... C07D 207/28; C07D 207/30
[58] Field of Search ................ 260/326.43, 326.2

[56] References Cited
UNITED STATES PATENTS

| | | | |
|---|---|---|---|
| 3,729,502 | 4/1973 | Beal et al. | 260/326.2 |
| 3,767,693 | 10/1973 | Samuelsson | 260/326.2 |

*Primary Examiner*—Dale R. Ore
*Attorney, Agent, or Firm*—Anthony P. Mentis

[57] ABSTRACT

Certain 1,5-disubstituted 2-pyrrolidinones, and their ring unsaturated analogs, resemble natural prostaglandins. The compounds are easier to prepare than the prostaglandins since they have at least one fewer center of asymmetry and accordingly fewer isomers are produced. Exemplary is 7-[2-oxo-5-(3-hydroxy-1-oct-1-enyl)-1-pyrrolidinyl]heptanoic acid of the formula:

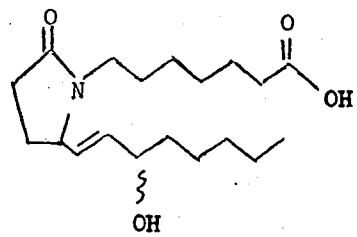

16 Claims, No Drawings

1,5-DISUBSTITUTED-2-PYRROLIDINONES, -3-PYRROLIN-2-ONES, AND -4-PYRROLIN-2-ONES

BACKGROUND OF THE INVENTION
1. Field of the Invention

This invention concerns substituted 2-pyrrolidinones, and their ring-unsaturated analogs, which resemble prostaglandins. The natural prostaglandins of the E, F and A series have several centers of asymmetry and are difficult to synthesize. The compounds of the present invention have at least one fewer center of asymmetry and are easier to prepare since fewer isomers are obtained.

2. Prior Art

Sedavkina et al, Khim, Geterotsikl. Soedin. 1972, (3), 331-2 have shown the preparation of 5-alkyl-N-($\beta$-hydroxyethyl)-2-pyrrolidinones from the corresponding $\gamma$-ketocarboxylate esters, ethanolamine and Raney nickel. These 2-pyrrolidinones are not the compounds of this invention.

STATEMENT OF THE INVENTION

There have now been discovered the prostaglandin-like compounds of the formula:

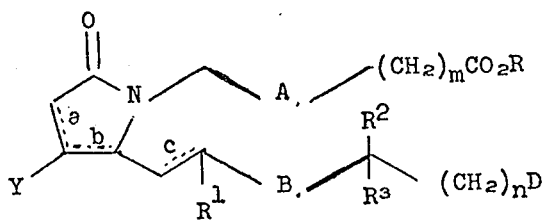

wherein

A is —CH=CH—, —C≡C—, —CH$_2$—, or —C$_6$H$_4$—(o, m, or p);
B is -CH$_2$—, >C=O or $$-\overset{|}{\underset{R^4}{C}}-OR^6;$$

D is —CH$_3$, —CF$_2$CH$_3$, or —CF$_3$;
Y is H or OR$^5$;
R is H, alkyl (straight or branched chain of 1–10 carbon atoms), cycloalkyl, aryl, aralkyl, alkaryl, or a physiologically acceptable cation;
R$^1$, R$^2$ and R$^3$ are individually H, CH$_3$ or C$_2$H$_5$;
R$^4$ is H, alkyl of 1–4 carbon atoms, vinyl or ethynyl;
R$^5$ and R$^6$ are individually H, CH$_3$, C$_2$H$_5$, tetrahydropyranyl (THP), benzyl, acyl of 1–4 carbon atoms or trialkylsilyl in which alkyl is straight or branched chain of 1–10 carbon atoms;
$m$ and $n$ are whole numbers in the range 1–8; $a$, $b$ and $c$ (the dotted lines) are optional additional bonds with the provisos that:
if $c$ is present, only of $a$ and $b$ is present;
if $c$ is absent, only one of $a$ and $b$ is present and A is not —C≡C—;
if $a$ or $b$ is present, Y is H;
if R is tert-butyl, Y is H, OTHP or trialkylsilyl and R$^6$ is not THP.

Terms used in the definition of R above include the following:

Cycloalkyl of 3–8 carbon atoms, including cyclopropyl, cyclobutyl, cyclopentyl, cyclohexyl, cycloheptyl and cyclooctyl.

Aryl of 6–14 carbon atoms, including particularly phenyl, halophenyl (halo = F, Cl, Br, I), sulfino-, sulfo-, sulfamoyl-, sulfanilyl-, sulfoamino- and sulfanilamidophenyl.

Aralkyl of 7–10 carbon atoms, including benzyl, phenethyl and 4-phenylbutyl.

Alkaryl of 7–10 carbon atoms, including tolyl, xylyl and duryl.

Physiologically acceptable cation, including particularly lithium, sodium, potassium, rubidium, cesium, ammonium and the many physiologically acceptable substituted ammonium cations such as triethylammonium, tetraethylammonium, tetrabutylammonium, tetrapropylammmonium and tris(hydroxymethyl)methylammonium.

The compounds of the above formula can be prepared by the following general scheme:

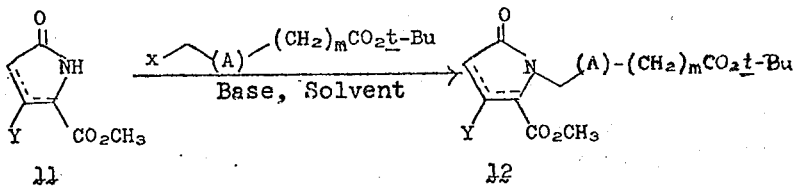

Y = H, tetrahydropyranyloxy or trialkylsilyloxy;
X = Br, I, tosyl or other leaving group. A leaving group is one which is readily displaceable from carbon in an exchange reaction. Other examples of such are chloride, methanesulfonate, p-nitrobenzene sulfonate and trifluoroacetate.

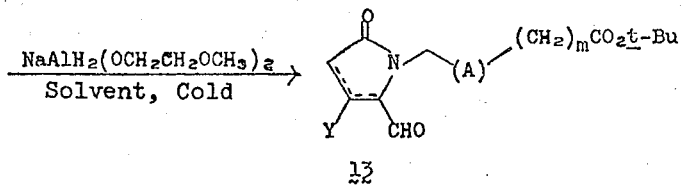

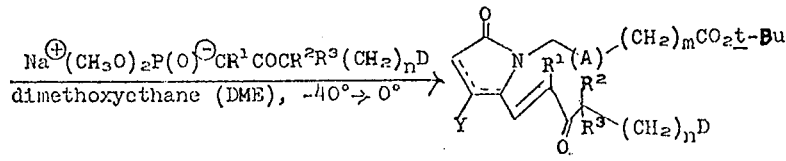

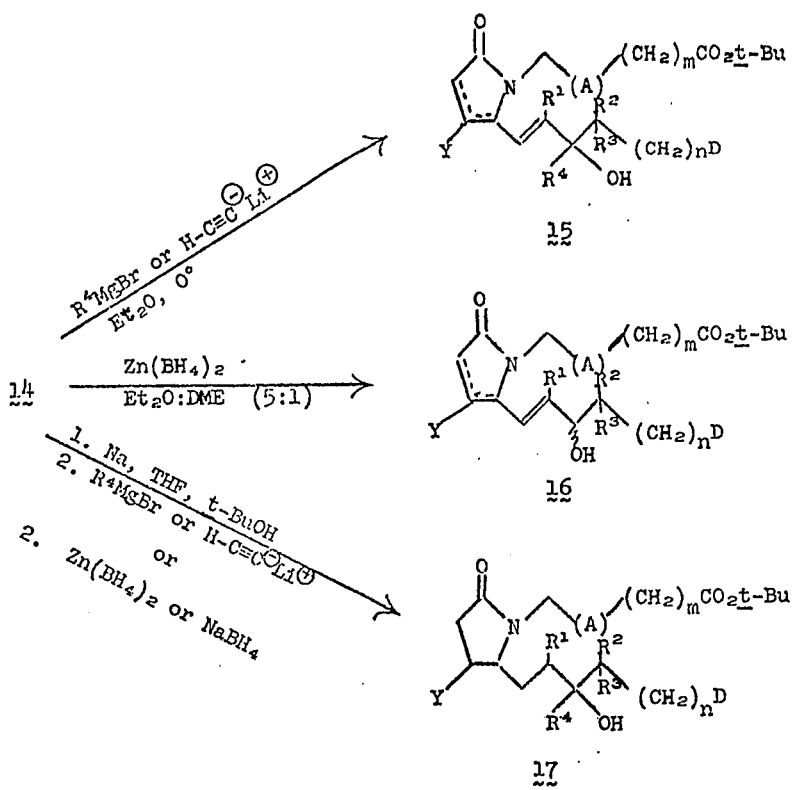
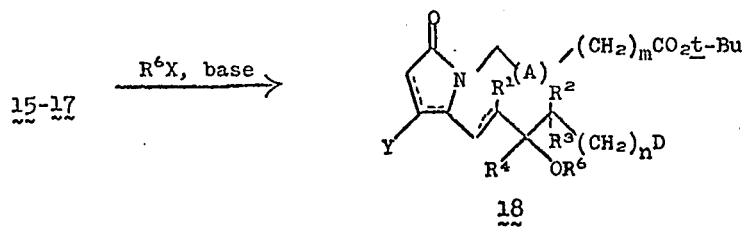
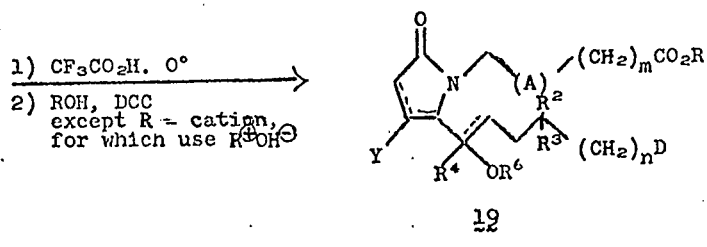
(DCC=dicyclohexylcarbodiimide)   Y = H or OH
In this step when Y on compound 18 is tetrahydropyranyloxy (OTHP) or trialkylsilyloxy, it becomes OH in compound 19.
In this step when Y on compound 19 is OH, it becomes $OR^5$ in compound 20.
Alternatively, particularly when $R^4$ is other than H,
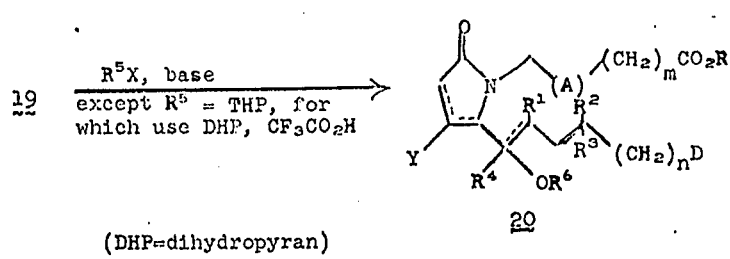
(DHP=dihydropyran)
the following sequence may be used to advantage:

15-17  1) DHP, CF$_3$CO$_2$H
2) NaOH, H$_2$O
3) ROH, DCC or R⊕OH⊖

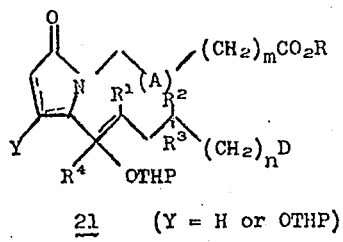

21  (Y = H or OTHP)

1) CH$_3$CO$_2$H or TsOH
2) R$^5$X, base (1 equiv.)
   (if Y ≠ H
3) R$^6$X, base (1 equiv.)

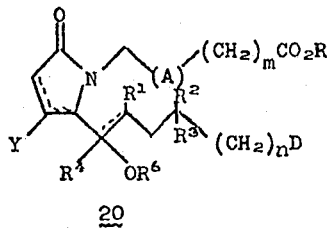

20

The compound of type 11 where Y = H and the optional double bond is not present is made by esterification of commercially-available pyroglutamic acid (see Ex. 1, Part A). The compound where Y = OTHP is made by heating the known dimethyl 3-hydroxy glutamate in alcohol, followed by treatment with dihydropyran and an acid catalyst (standard conditions for the preparation of a tetrahydropyranylated alcohol):

If, rather than being treated with dihydropyran, the intermediate cyclic alcohol is dehydrated (by treatment with strong base, dicyclohexylcarbodimide, or mesyl chloride sulfur dioxide, for example), or converted to, for example, the corresponding bromide (using PBr$_3$ or triphenylphospine dibromide) followed by dehydrohalogenation, compound 11 with Y = H and the optional double bond present is produced:

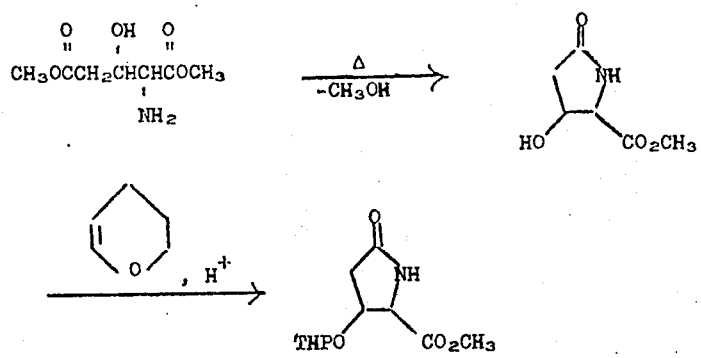

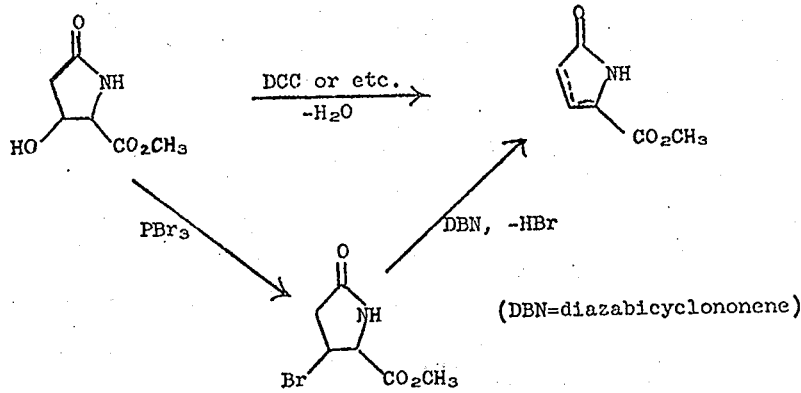

(DBN=diazabicyclononene)

As the product is a mixture in which the predominance of a particular double bond isomer depends on the precise elimination conditions, the double bond is represented as a dotted line. The compounds are separable but need not be separated for subsequent reaction.

The lactams 11 are then N-alkylated with $XCH_2(A)$-$(CH_2)_mCO_2$t-Bu using sodium hydride as the base and dimethylformamide as the solvent. Other base/solvent systems can be used. The alkylating agents $XCH_2(A)$-$(CH_2)m$—$CO_2$t-Bu where $X = Br$ and $A = CH_2$ are made by the standard method [e.g., A. L. McCloskey et al., Org. Syn. Coll., Vol. 4, 261 (1963)] from the commercially-available $\omega$-bromo acids and isobutene. The compounds where $A = -C \equiv C-$ are made by the same esterification technique from the corresponding $\omega$-bromo alkynoic acids. These acids are prepared by the method of Ferdinandi and Just [Can. J. Chem., 49, 1070 (1971)] from commercially-available materials. Reduction of these tert-butyl $\omega$-haloalkynoates with hydrogen over Lindlar catalyst [H, Lindlar, Helv. Chim, Acta, 35, 446 (1952)] or, preferably, the Cram modification of it [D. J. Cram and N. L. Allinger, J. Am. Chem. Soc., 78. 2518 (1956)] gives the compound with $A = -CH=CH-$ in the desired cis-modification. Alternatively, Brown's P-2 nickel boride catalyst [H. C. Brown and C. A. Brown, J. Am. Chem. Soc., 85, 1005 (1963)] may be used for this purpose.

The compounds where $A = o$ or $p$-phenylene are prepared by bromomethylation of the commercially-available $\omega$-arylalkanoic acids. This transformation is accomplished by treatment of the acid with hydrogen bromide and formaldehyde (as paraformaldehyde) under standard conditions (see, for example, Organic Reactions, Vol. I, Chap. 3, p. 72, John Wiley and Sons, N.Y., 1942), producing both the ortho and para isomers which are, however, readily separable. Best yields of the bromomethylated products are obtained when the reaction is carried out in the absence of added zinc salts.

The choice of $X = Br$ for the alkylating agents is made on the basis of ease of preparation and ready displaceability. With $X = Cl$ the compounds are considerably less reactive, while $X = I$ (prepared from the compounds with $X = Br$ by the Finkelstein halide interchange reaction) are somewhat more difficult to prepare and to handle. The bromine atom can be displaced by hydroxide and the resulting alcohol converted to its toluenesulfonate or methanesulfonate derivative for displacement, but little would be gained by these additional steps.

In the alkylation reaction by which compounds of type 11 are converted to compounds of type 12, the base employed is preferably a nonnucleophilic base with a pKb of 19 or greater. Such bases include the hydrides of the alkali metals, particularly Li, Na, K, Rb and Cs; alkali metal alkyls such as methyllithium; alkali metal triarylmethides such as potassium triphenylmethide and hindered alkali metal amides and alkoxides such as lithium diisopropylamide and potassium tert-butoxide.

To avoid undue loss of base in side reaction with water, it is preferred that the reactants and solvent be reasonably anhydrous. Solvent used as reaction media should be inert to the reactants and products. Suitable media include polar aprotic organic solvents such as dimethylformamide, hexamethylphosphoramide, tetramethylenesulfone, and ethers such as dimethyl ether, diethyl ether, dimethoxyethane and tetrahydrofuran.

The molar proportions in which the lactam, alkylating agent and base are brought together are not critical, since any proportion in which all three are brought together will yield at least some of the corresponding compound of type 12. Best yields are obtained using substantially equimolar proportions of alkylating agent and base with a slight molar excess of lactam 11. Temperatures in the alkylation reaction range from $-50°$ to $140°C$. and temperatures in the range from $-50°$ to $120°C$. are preferred. Pressure is not a critical variable and pressures both above and below atmospheric pressure may be employed.

Reduction of the 5-carbomethoxy group in 12 to the 5-formyl group in 13 is accomplished by the use of the selective, soluble reducing agent sodium bis(2-methoxy-ethoxy) aluminum hydride, developed by J. Vit [Eastman Organic Chem. Bull., 42 (3), 8 (1970)] and marketed by Eastman as an 80% solution in benzene under the tradename Vitride. With this reducing agent, the carbomethoxy group is reduced while the carbotert-butoxy group is not. The tert-butyl group protection of the terminal carboxyl moiety is presently viewed as unique in providing both resistance to nucleophilic displacement in the conversion of 11 to 12 and resistance to reduction in the conversion of 12 to 13 while being relatively easily removed when desired (conversion of 18 to 19). The reducing agent also seems to offer a unique combination of selectivity and ease of handling. Use of other reducing agents such as lithium aluminum hydride would necessitate inconveniences such as inverse addition and low solubility while not promising any improvement in selectivity.

In the reduction reaction by which esters of type 12 are converted to aldehydes of type 13 by the action of the reducing agent $NaAlH_2(OCH_2CH_2OCH_3)_2$, the reactants and solvent are preferably substantially anhydrous to avoid loss of the reducing agent in a side reaction with water. The solvent should be liquid, capable of dissolving the reactants at the reaction temperature and inert to the reactants and products. Low melting ethers such as dimethyl ether, diethyl ether and tetrahydrofuran are preferred as solvents.

The molar proportions in which the ester of type 12 and the reducing agent may be brought together in the reduction reaction is not critical, since any proportions in which the two are brought together will yield at least some of the product aldehyde of type 13. It is preferred to employ either equimolar quantities or a slight molar excess of the ester of type 12. The temperature for the reduction reaction should range from $-90°$ to $-40°C$. and temperatures in the range from $-90°$ to $-50°C$. are preferred. Pressure is not a critical veriable and pressures both above and below atmospheric pressure may be used.

The conversion of 13 to 14 is accomplished by the Emmons modification of the Wittig reaction [W. S. Wadsworth, Jr. and W. D. Emmons, J. Am. Chem. Soc., 83, 1733 (1961)], first shown to be useful for prostaglandin synthesis by Corey [E. J. Corey et al., J. Am. Chem. Soc., 91, 5675 (1969)]. The phosphonates are not unique in their usefulness for this type of conversion (the more usual phosphine-type Wittig reagents can and have been used), but they are easy to use and give high yields of specifically the transolefinic product 14. The phosphonates, $(CH_3O)_2P(O)CHR^1COCR^2R^3(CH_2)_nD$, can be made by any one of three methods, that of Arbusov [B. A. Arbusov, Pure Appl. Chem., 9, 307 (1964)], Corey [E. J. Corey and G. T. Kwiatkowski, J. Am. Chem. Soc., 88, 5654 (1966)] or Grieco [P. A. Grieco and R. S. Finkelhor, J. Org. Chem., 38, 2909 (1973)]. The Corey method is preferable because the necessary starting materials are most readily available.

The conversion of 13 to 14 is best done at reduced temperature to avoid side-reactions such as self-condensation of the aldehyde molecules. Use of a large excess of phosphonate salt would also accomplish this purpose, but with loss of convenience and economy.

The α,β-unsaturated ketones 14 provide a branch point in the synthesis. Reaction of the ketone carbonyl with Grignard reagents provides the tertiary allylic alcohols 15. Alkyl lithium reagents corresponding to the Grignards would be expected to give similar results but also more extensive side-reactions due to their higher inherent reactivity. For $R^4$ = ethynyl the ketone is reacted with ethynyllithium (preferably as its ethylenediamine complex). Ethynylsodium can also be used, but it is somewhat less suitable due to its greater tendency toward conjugate addition.

For $R^4$ = H, reduction of the unsaturated ketone to the allylic alcohol is best accomplished with zinc borohydride, a reagent first described by Gensler [W. J. Gensler et al., J. Am. Chem. Soc., 82, 6074 (1960)]. Other complex metal hydrides in general are either too reactive (e.g., lithium aluminum hydride) or give extensive conjugate reduction (e.g., sodium borohydride). If an optically active alcohol is desired, a highly hindered optically active borane such as that described by Corey [E. J. Corey et al., J. Am. Chem. Soc., 94, 8616 (1972)] is used to advantage for this reduction. Finally, if it is desired that optional bond (c) not be present, the double bond conjugated to the ketone carbonyl can be reduced using sodium metal dissolved in tetrahydrofuran with tert-butanol added (for discussion see: H. O. House, "Modern Synthetic Reactions", W. A. Benjamin, Menlo Park, California, 1972, p. 145 ff). Such a reaction also reduces double bond (a) or (b) should it be present and converts A = —C ≡ C— to a trans double bond and is therefore not suitable if these changes are not desired. The resulting saturated ketone is then treated just as the unsaturated one was, converting it to a tertiary alcohol by treatment with a Grignard reagent or ethynyllithium or to a secondary alcohol by reduction. In this case zinc borohydride is unnecessary, since conjugate reduction is no problem, and more readily-available sodium borohydride may be employed.

Should it be desired that $R^6$ be other than H, the alcohol is treated with an alkylating or acylating agent in the presence of a base. Alkylation is simply an example of the classical Williamson ether synthesis using a tertiary alkoxide as the base and methyl iodide, ethyl iodide, or a benzyl iodide as the alkylating agent. Acylation would be accomplished by using the desired acyl chloride and an equivalent of a tertiary amine or metal carbonate or oxide to neutralize the liberated hydrogen chloride.

Treatment of compound 18 ( or 17, if $R^6$ is to remain H) with anhydrous trifluoroacetic acid cleaves the tert-butyl ester group so the terminal carboxyl group can be esterified with another alcohol. Cleavage of the tert-butyl group is also accomplished with strongly acidic catalyst such as hydrogen chloride in moist chloroform or boron trifluoride etherate if desired, but the temperature during the cleavage should remain at 0°C or below in order to minimize elimination of the —$OR^6$ group. The final esterification of the carboxyl group is accomplished by the use of an excess of the alcohol ROH and dicyclohexyl carbodiimide as the esterification reagent. Other esterification reagents can be used, such as carbonyldiimidazole or thionyl chloride.

Finally, if Y = —OH and it is desired that $R^5$ not be H, 19 is treated in the same manner as 15–17 with an alkylating or acylating agent and the appropriate base.

Specific Embodiments of the Invention

In the illustrative examples which follow, parts and percentages are by weight unless otherwise indicated.

EXAMPLE 1

Part A - Tert-butyl 7-(2-Oxo-5-methoxycarbonyl-1-pyrrolidinyl) heptanoate (1)

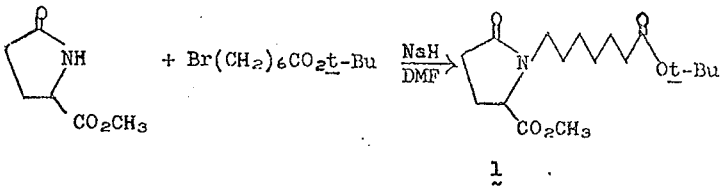

Into a thoroughly dried 500 ml flask filled with dry nitrogen was placed 5.0 g of 57% sodium hydride/oil dispersion (2.85 g of sodium hydride, 0.120 mole). The dispersion was washed three times with 10 ml portions of dry petroleum ether, then dried under a nitrogen stream. To the dry hydride was added 200 ml of dimethylformamide (distilled from calcium hydride, stored over 4A molecular sieves) with stirring (magnetic spinbar). To the suspension was added dropwise over 15 minutes a mixture of 16.0 g of methyl pyroglutamate (0.112 mole) and 28.0 g of tert-butyl 7-bromoheptanoate (0.105 mole) in 30 ml of dry dimethylformamide. After the addition was complete, the mixture was left to stir at ambient temperature for about 63 hours. The reaction was fairly vigorous, forming a dark green solution which gradually became yellow-brown. The reaction mixture was poured into a well-stirred mixture of 1200 ml of water and 300 ml of diethyl ether, separated, and the aqueous phase extracted twice more with 200-ml portions of ether. The ethereal extracts were combined, washed three times with 300-ml portions of water, once with 200 ml of saturated sodium chloride solution and dried over magnesium sulfate/calcium sulfate. Removal of the ether (rotary evaporator) gave 28.8 g of a light yellow oil, which was distilled (short-path apparatus: 152°–155°/0.3 μ Hg) to yield 26.2 g (76%) of 1 as a colorless oil. IR: 1750, 1740, 1700, 1415, 1395, 1385, 1210, 1155 cm$^{-1}$; pmr: δ 4.25 (m, 1), 3.76 (s, 3), 3.55 (m, 1), 2.95 (m, 1), 2.22 (m, 1), 1.46 (s) and 1.40 (broad m, 17 total).

Part B - Tert-butyl 7-(2-Oxo-5-formyl-1-pyrrolidinyl)heptanoate (2)

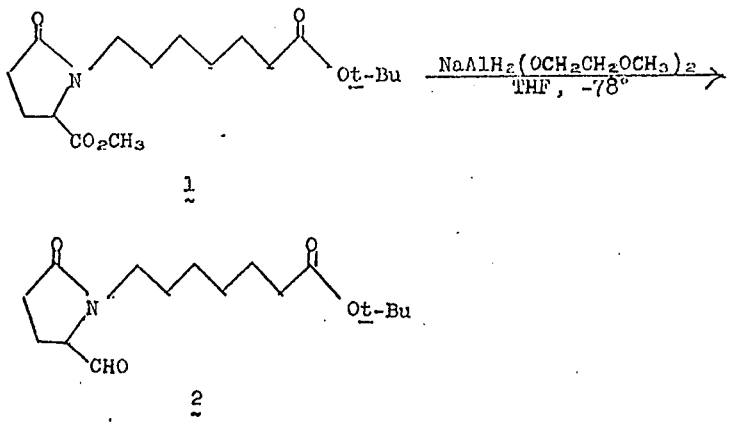

To a solution of 10.00 g of diester lactam 1 (30.5 mmoles) in 200 ml of dry tetrahydrofuran (THF) under nitrogen at −78°C was added dropwise a solution of 5 ml of "Red-Al" (70% solution of sodium bis(2-methoxyethoxy) aluminum hydride in benzene, Aldrich Chemical Company) followed by an additional 10 ml of THF. The mixture was stirred 72 hours at −78°C and poured cold into a mixture of 500 ml of water and 300 ml of ether. After another 30 minutes of stirring, the organic phase was separated, washed three times with water, once with saturated NaCl and dried over magnesium sulfate/calcium sulfate. The oil obtained after evaporation of the ether was heated 0.5 hour at 100°C/0.001 Torr to remove water and then distilled to yield 4.89 g (54% yield) of 2 in the form of a yellow mobile oil. pmr: δ 9.58 (d, J = 2.5 Hz, 1), 4.2 (m, 1), 2.8–3.8 (broad m, 2), 2.3 (m, 6), 1.45 (s and broad m, 17). A larger sample of 2 prepared essentially by scaling up the above procedure gave the following additional measurements. IR: 1720, 1660, 1640 (sh), 1450, 1415, 1385, 1360, 1250, 1150, 1100, 845 cm$^{-1}$. High-resolution mass spectrum: M + meas. m/e 268.1918; calcd for $C_{15}H_{26}NO_3$: 268.1911.

The larger sample was dried by azeotropic distillation of a benzene solution. The material thus obtained was satisfactory for further reaction, thus substantially increasing the yield of product which is temperature-sensitive and was partially destroyed on distillation.

Part C - Tert-butyl 7-[2-Oxo-5-(3-oxo-1-oct-1-enyl)-1-pyrrolidinyl] heptanoate (3)

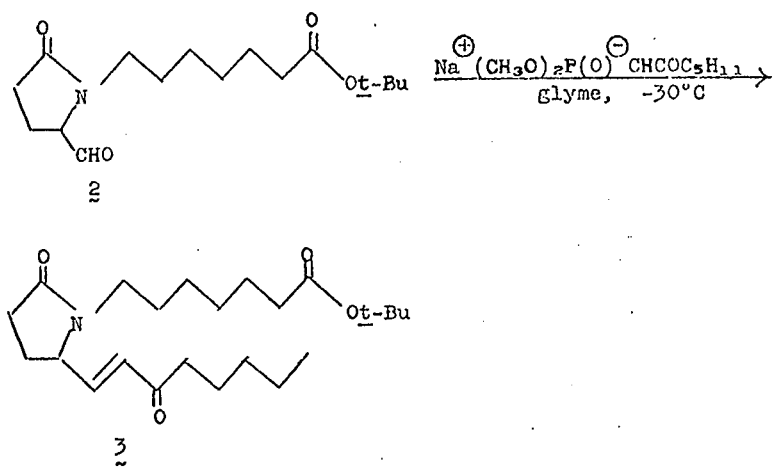

To a solution of 0.724 g of dimethyl (2-oxohepytyl)-phosphonate and 0.137 g of a 57% mineral oil dispersion of sodium hydride (Callery Chemical Company) in about 200 ml of ethylene glycol dimethyl ether (glyme) at −30°C was added 1.00 g of aldehyde 2. The mixture was stirred for 3 hours at −25°C and then drowned in water. The resulting mixture was extracted with ether. The ether extract was dried over anydrous magnesium sulfate/calcium sulfate and chromatographed on silica gel to obtain 0.870 g of the unsaturated ketone 3 in the form of a colorless oil (66% yield). It showed ir absorption at 990 cm$^{-1}$ and pmr: δ 6.63 (d of d, J = 7.5 and 17 Hz, 1), 6.20 (d, J = 17 Hz, 1), 4.24 (m, 1) 3.6 (broad m, 1), 2.3 (broad m, 10), 1.45 (s, 9), 1.4 (broad m, 6), 0.90 (broad t, J = 6 Hz, 3). High-resolution mass spectrum: M+ meas. m/e 337.2215; calcd for $C_{19}H_{31}O_4N$: 337.2251.

EXAMPLE 2

Tert-butyl
7-[2-Oxo-5-(3-hydroxy-1-oct-1-enyl)-1-pyrrolidinyl]-
heptanoate (4)

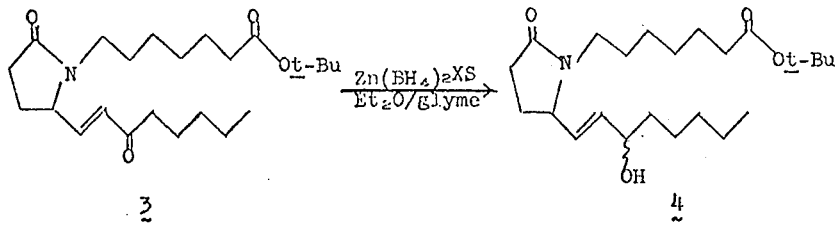

In 50 ml of a 5:1 mixture of diethyl ether, glyme under nitrogen was dissolved 2.00 g of ketone 3 (5.08 mmoles) and the solution was heated to reflux. To this solution was added 28.2 ml of ca. 0.45M zinc borohydride/ether solution (10.0 equiv.) by syringe and reflux was continued for 2.5 hours. The solution became cloudy within 5 minutes and remained so throughout the reaction. The reaction mixture was then poured into a stirred mixture of 150 ml of ether/150 ml of water. The reaction flask was rinsed out with this mixture. To the ether/water mixture was added sufficient saturated aqueous ammonium chloride solution to dissolve the precipitated zinc salts. The layers were separated and the aqueous layer was extracted with an additional 100-ml portion of ether. The ethereal extracts were combined, washed three times with water, once with saturated sodium chloride solution and dried over magnesium sulfate/calcium sulfate. The solution was filtered and concentrated (rotary evaporator) to give 1.817 g of 4 (90%) as a light yellow oil. IR: 3400 (broad), 1725, 1680, 1455, 1415, 1388 (sharp), 1365, 1255, 1150, 970 (trans—CH=CH—), 850 cm$^{-1}$; nmr: δ 5.63 (m, strong secondary coupling effects, 2), 4.1 (broad m, 2), 3.03 (broad, 1), 2.2 (broad m, 8), 1.45 (s, 9), 1.4 (broad m, 16), 0.88 (broad t, 3). High-resolution mass spectrum: M$^+$ meas. m/e 395.2901; calcd for $C_{23}H_{41}NO_4$: 395.3035.

EXAMPLE 3

7-[2-Oxo-5-(3-hydroxy-1-oct-1-enyl)-1-pyrrolidinyl]-
heptanoic Acid (5)

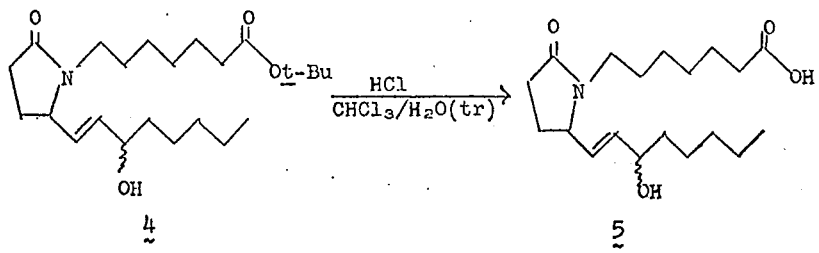

Ester 4 (0.280 g, 0.71 mmole) was dissolved in 20 ml of chloroform. To the solution was added 2-3 drops of water. Hydrogen chloride gas was passed into the vigorously stirred mixture over a 90-minute period, with chloroform added periodically to maintain the solvent level. During the reaction period the mixture became cloudy and yellow. The reaction mixture was then concentrated on a rotary evaporator and the resulting oil was taken up in 20 ml of ether. The ethereal solution was extracted three times with 20-ml portions of 5% sodium bicarbonate solution. The bicarbonate extracts were combined, acidified (ca. pH 2) with concentrated hydrochloric acid and the resulting milky suspension extracted three times with 20-ml portions of ether. The ethereal extracts were combined, washed three times with water, once with saturated sodium chloride solution and dried over magnesium sulfate/calcium sulfate. Evaporation of the ether gave 0.212 g of crude 5 (88%) as a light yellow oil. The oil was taken up in ca. 2 ml of ethyl acetate from which it crystallized upon standing three days in a −30°C freezer. The white, microcrystalline powder (0.170 g, 71%) melted over the range 83°–97°C, not unusual for a mixture of diastereomers. Some of the crystals were observed to melt as high as 103°C, however, so that there is a possibility that repeated crystallizations from more dilute solution might effect a separation of the two compounds. IR (CHCl$_3$): 3600–2400 (—CO$_2$H and —OH), 1720 (broad), 1665, 1455, 1415, 1375, 1205 (broad), 1160 (broad), 975 cm$^{-1}$ (trans—CH=CH—); nmr: δ8.38 (broad s, -CO$_2$H and —OH with intramolecular exchange, 2), 5.6 (m, 2), 4.12 (broad m, 2), 2.3 (broad m, 6), 1.38 (broad m, 18), 0.9 (broad t, 3). High-resolution mass spectrum of bis-tri-methylsilylated derivative, M$^+$ meas. m/e 468.2981; calcd for $C_{24}H_{46}O_4NSi_2$, 468.2963.

EXAMPLE 4

Tert-butyl
7-[2-Oxo-5-(3-hydroxy-3-methyl-1-oct-1-enyl)-1-pyrrolidinyl]heptanoate (6)

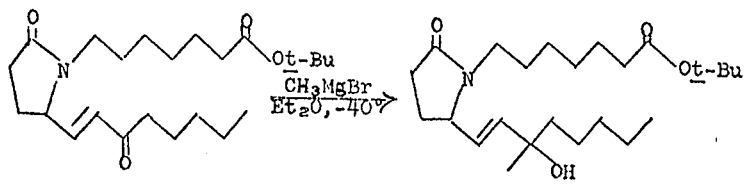

Into a thoroughly dried 50-ml three-neck round bottom flask under nitrogen equipped with a magnetic stirring bar was injected via rubber serum cap a solution of 200 mg of ketone 3 (9.495 mmoles) in 10 ml of anhydrous diethyl ether. The solution was cooled to −40°C and 1.0 equivalent methylmagnesium bromide solution in ether (0.19 ml of 2.6 M solution) was added, causing immediate formation of a white precipitate. The mixture was left to stir overnight, coming to −25°C. During this time the ether evaporated leaving a white solid adhering to the flask. The contents of the flask were taken up in 20 ml of ether and 30 ml of water and transferred to a separatory funnel where the mixture was neutralized (not acidified) with 3 drops of glacial acetic acid. The organic phase was separated, washed twice with water, dried over anhydrous sodium sulfate and concentrated on a rotary evaporator to yield 0.194 g of crude 6 (93.5%) as a light yellow oil. Analysis of the product by thin-layer chromatography (Silica gel G/ethyl acetate) showed mainly one spot, $R_f$ 0.35, with the other spots being barely discernible. IR: 3400 (broad, —OH), 1725 (ester CO), 1670 (amide CO), 1455, 1420, 1390 (sharp), 1365, 1255, 1155, 975 (trans—CH=CH—), 850 cm$^{-1}$; nmr:δ5.67 (m, 2), 4.05 (broad m, 1), 2.3 (broad m, 6), 1.62, 1.28 and 1.6-1.1 (—C(CH$_3$)$_3$, —CH$_3$, and -CH$_2$'s superimposed, —21), 0.88 (broad t, 3). High-resolution mass spectrum, M$^+$ meas. m/3 409.3202; calcd for C$_{24}$H$_{43}$O$_4$N: 409.3190.

The compounds of this invention mimic or antagonize the prostaglandins. The apparent contradiction in this statement is resolved by considering the fact that PGE$_1$, a natural prostaglandin, reverses or antagonizes the contracting action of PGF$_{2\alpha}$, another prostaglandin, or bronchial smooth muscle. In a similar manner, compound 5 (Example 3) contracts rat uterine smooth muscle (at 50 ng/ml) in the same way as PGE$_1$ and is antagonized in this action by compound 4 Example 2). Compound 4 (the tert-butyl ester of 5) also antagonizes PGE$_1$-induced smooth muscle contractions (at 10μg/ml for 50% inhibition). Both compounds 4 and 5 are, however, active as topical and injectable antiinflammatory agents with nearly the same level of activity. This type of behavior is believed to be related to prostaglandin antagonism. Thus, any of the compounds may be both a prostaglandin mimic and a prostaglandin antagonist depending on the biological system being considered.

The acid 5 has shown activity both as a topical antiinflammatory agent (against croton oil-induced inflammation of rat and mouse ears at 2–3 mg/ear) and as a systemic antiinflammatory agent (as an intraperitoneal injection against adjuvant-induced arthritis in rats at 50 mg/kg). The ester 4 is also active, though slightly less so, in both of these tests. This activity is thought to stem from antagonism to indigenous prostaglandins, implicated as primary mediators of inflammation.

Compound 5 has shown activity in cutting off gastrin-induced gastric acid secretion (suggesting utility as an antiulcerogenic medicament) and as an antagonist to histamine-induced bronchoconstriction (suggesting utility as a bronchodilator/antiasthmatic drug).

Other utilities cited for prostaglandins and the present prostaglandin analogs include use as hypotensives, blood platelet aggregation inhibitors, nasal decongestant, antifertility agents, abortifacient and parturition agents, sedatives, analgesics, and spasmolytics.

Using the general scheme described in detail above a series of tables of examples has been constructed on the following basis:

Three representative starting materials were chosen for column A. All three are methyl esters mostly for convenience and ease of preparation — the ethyl or propyl esters would do as well. Compound (c) is shown with two partial double bonds to indicate that it is a mixture of the two possible isomers.

The compounds of column B, which are to be combined with those of A in the manner shown in the general scheme, are all bromides, again as a matter of convenience and ease of preparation. The iodides, or the methanesulfonate or toluenesulfonate derivatives of the corresponding alcohols, and possibly the chlorides, are equally useful in this reaction. All of the compounds are tertiary butyl esters because this functionality combines ease of preparation with resistance to the reducing conditions of the next reaction and is thus more or less unique in this respect.

Combination of each of the compounds of column A with each of the compounds of column B gives the compounds of column C.

Reduction of each of the compounds of column C with sodium bis(2-methoxyethoxy) aluminum hydride in tetrahydrofuran at −78°C gives each of the compounds of column D. Other reducing agents, e.g., diisobutyl aluminum hydride, lithium aluminum hydride or aluminum hydride, might be useful, but offer no advantage.

Combining each of the compounds of column D with each phosphonate reagent or reagents entered under the corresponding letter in column E gives the compounds of column F. Thus, for example, the compound of entry (a), column D, is combined with the compound of entry (a) 1., column E, to give the compound of entry (a), column E. Compound (a), column D, with compound (a)2., column E, gives compound (b), column F. The compounds of column E are all dimethyl phosphonates as a matter of convenience, ease of synthesis and availability of the necessary precursors. Other dialkyl (and possibly diaryl) phosphonates are equally useful for this reaction. The triaryl- or trialkylphosphonium halide-type Wittig reagents, e.g., O$_3$P$^+$-CH$_2$CO(CH$_2$)$_4$CH$_3$Br$^-$, are also useful in this transformation, but with some loss in convenience of use and ease of preparation.

Treatment of each of the compounds of column F with the reagent or reagents listed under the same letter in column G gives each of the compounds of column H. Zinc borohydride was chosen as the standard reducing agent because it is relatively easy to make and use and relatively free of the objectionable side-reaction (unlike, for instance, sodium borohydride) of reduction of the double bond conjugated to the ketone moiety. Highly sterically-hindered and/or optically active boranes are also useful, particularly for the production of a single absolute configuration. Lithium tri-t-butoxy aluminum hydride or aluminum hydride are not as convenient or selective in this reduction. Catalytic reduction can be used, but only at the expense of other sites of unsaturation in the molecule. The use of a dissolving metal reagent, sodium-tetrahydrofuran (THF)-tert-butanol (t-BuOH), is illustrated in certain examples for the reduction of the α,β-unsaturated ketone moiety to the saturated alcohol. This reagent can be substituted for by lithium-THF-t-BuOH of lithium-liquid ammonia, but with some loss in selectivity. Acetylenic (—C ≡ C—) linkages and unsaturations in the pyrrolidone ring are reduced by this reagent and are thus incompatible with its use in this synthesis. The Grignard reagents shown in column G are the alkyl magnesium bromides for convenience and ease of preparation. The corresponding chlorides and iodides are equally useful. The corresponding alkyl lithium reagents are less useful because they are inherently much more reactive and thus less selective than the Grignard reagents. An exception to this is the acetylenic lithium reagent which is the material of choice for alkynylations.

Treatment of each of the compounds of column H with the alkylating or acylating agent $R^6X$ (X = I for alkylating agents and = Cl for acylating agents) and appropriate base shown in column I yields the compounds of column J.

The compounds of column J, when treated with trifluoracetic acid at 0°C lose isobutene to give the corresponding acids (R = H). If this is the desired product, no entry is made in column K. Other strongly acidic catalysts can also be used, but care must be exercised so as to not cause dehydration if $R^6$ = H. A strongly acidic ion-exchange resin such as one of the Dowex 50-X series is useful for this transformation. [Since tetrahydropyranyl ethers are liable under the conditions necessary to remove the tert-butyl group, all the entries in column J with Y = —OTHP give entries in column L with Y = —OH.] If it is desired that R be other than H, the acids are treated with the alcohol ROH or the salt $R^+OH^-$ or $R^+Cl^-$ and, in the case of the alcohols, an esterification catalyst such as dicyclohexylcarbodiimide, carbonyldiimidazole or thionyl chloride. If the salts $R^+Cl^-$ are used, an equivalent of nonnucleophilic base, such as triethylamine or a metal carbamate or oxide, is also used to take up the liberated hydrogen chloride. The alcohol or salt are shown in column K, but the catalyst or base are omitted. The products of the esterification or neutralization are shown in column L.

Finally, if Y = —OH and it is desired that $R^5$ be other than H, the compounds of column L are alkylated or acylated as described above for column J with the reagents shown in column M to give the entries in column N. In addition, dihydropyran and an acid catalyst can be used if $R^5$ = THP is desired.

TABLE I

| | A | | B |
|---|---|---|---|
| a) | (pyrrolidinone with $CO_2CH_3$) | a) | $BrCH_2(CH_2)_5CO_2t\text{-Bu}$ |
| | | b) | $BrCH_2C \equiv C(CH_2)_3CO_2t\text{-Bu}$ |
| b) | (pyrrolidinone with THPO and $CO_2CH_3$) | c) | $BrCH_2CH=CH(CH_2)_3CO_2t\text{-Bu}$ |
| | | d) | $BrCH_2CH_2CO_2t\text{-Bu}$ |
| c) | (dihydropyrrolone with $CO_2CH_3$) | e) | $BrCH_2CH=CH(CH_2)_6CO_2t\text{-Bu}$ |
| | | f) | $BrCH_2$–(C$_6$H$_4$)–$(CH_2)_2CO_2t\text{-Bu}$ |

| | C | | D |
|---|---|---|---|
| a) | (pyrrolidinone, N$(CH_2)_6CO_2t\text{-Bu}$, $CO_2CH_3$) | a) | (pyrrolidinone, N$(CH_2)_6CO_2t\text{-Bu}$, CHO) |
| b) | (pyrrolidinone, NCH$_2$C≡C(CH$_2$)$_3$CO$_2$t-Bu, $CO_2CH_3$) | b) | (pyrrolidinone, NCH$_2$C≡C(CH$_2$)$_3$CO$_2$t-Bu, CHO) |

TABLE I-continued
c) 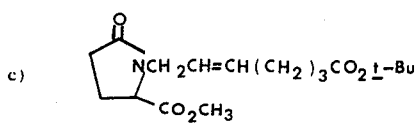　　c) 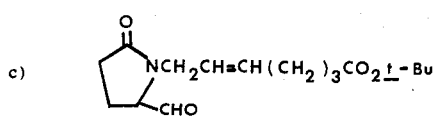
d) 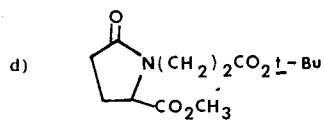　　d) 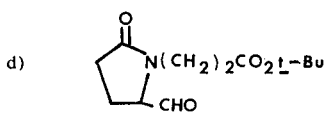
e) 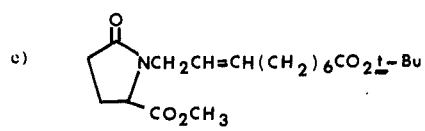　　e) 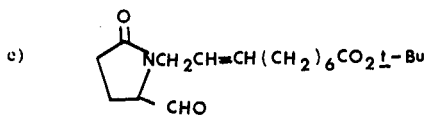
f) 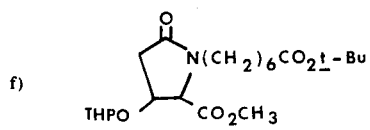　　f) 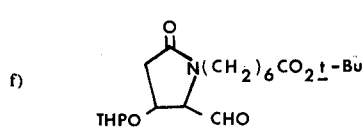
g) 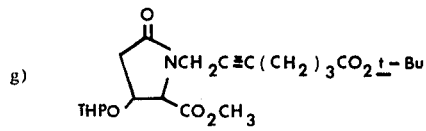　　g) 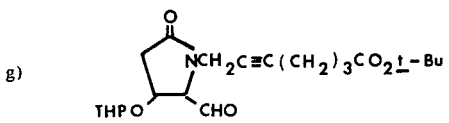
h) 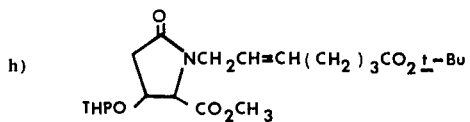　　h) 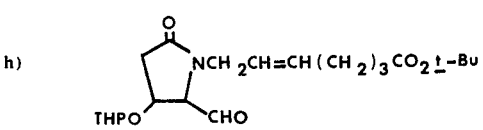
i) 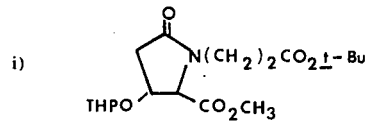　　i) 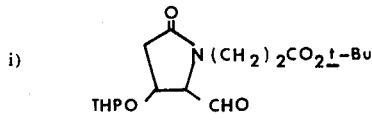
j) 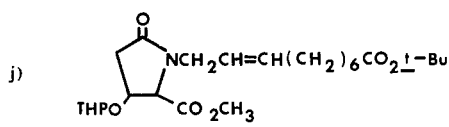　　j) 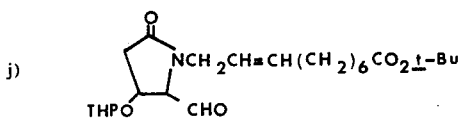
k) 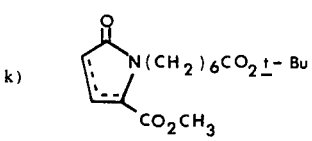　　k) 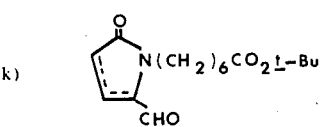

TABLE I-continued
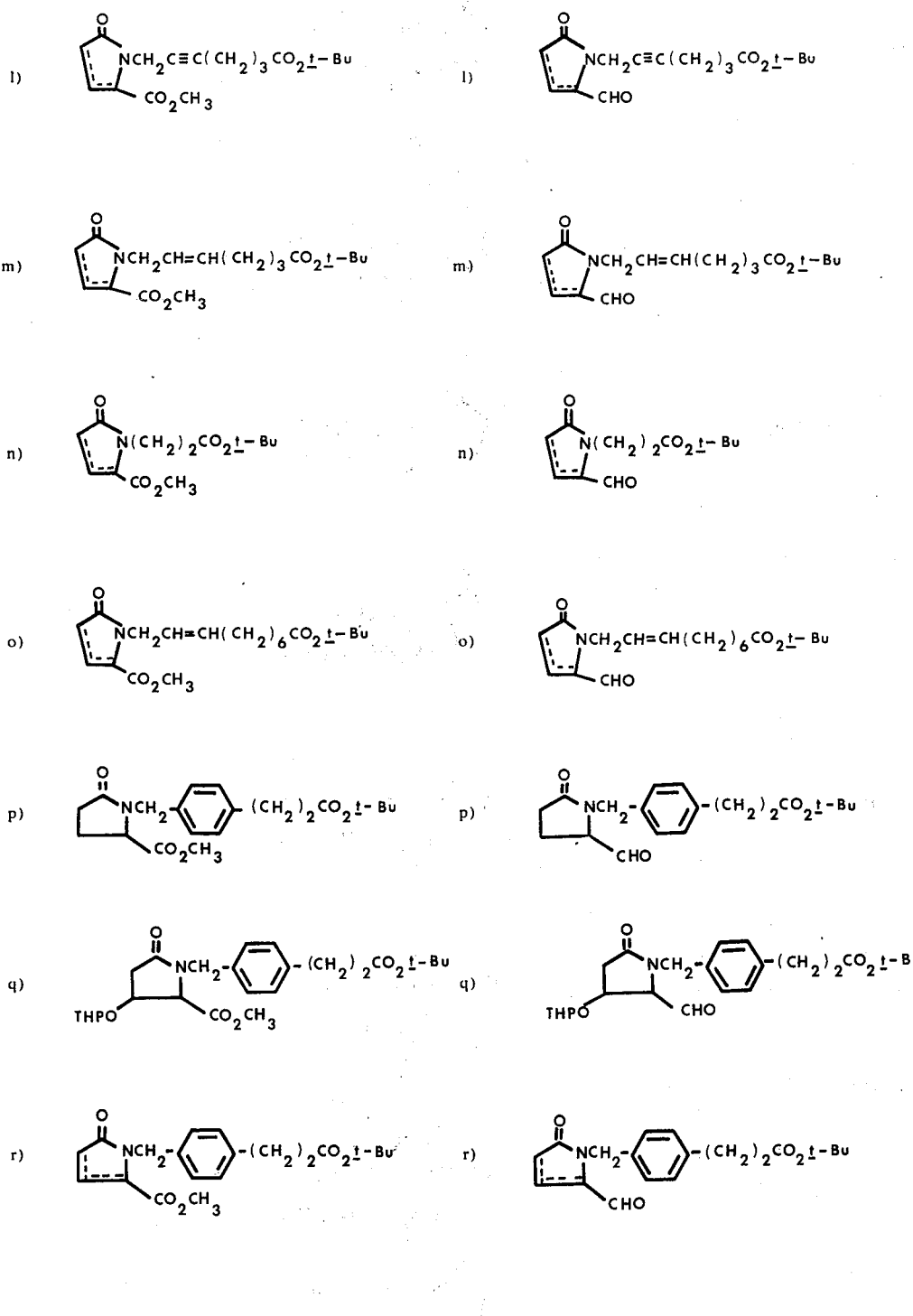
| | E | | F |
|---|---|---|---|
| a) | 1. $(CH_3O)_2P(O)CH_2CO(CH_2)_4CH_3$ | a) | 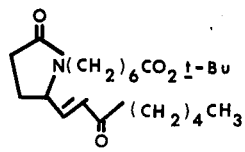 |

TABLE I-continued
| | | |
|---|---|---|
| 2. $(CH_3O)_2P(O)CH_2COC(CH_3)_2(CH_2)_3CH_3$ | b) | 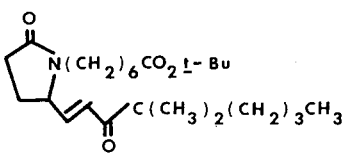 |
| 3. $(CH_3O)_2P(O)CH_2CO(CH_2)_4CF_3$ | c) | 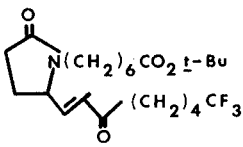 |
| 4. $(CH_3O)_2P(O)CH_2CO(CH_2)_3CF_2CH_3$ | d) | 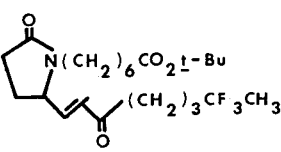 |
| 5. $(CH_3O)_2P(O)CH_2CO(CH_2)_8CH_3$ | e) | 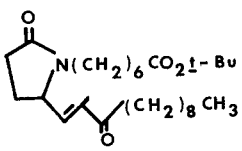 |
| b) 1. $(CH_3O)_2P(O)CH_2COC(CH_3)_2(CH_2)_3CF_3$ | f) | 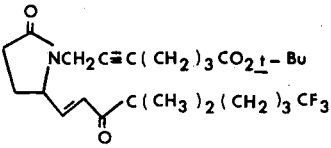 |
| 2. $(CH_3O)_2P(O)CH(CH_3)CO(CH_2)_6CF_2CH_3$ | g) | 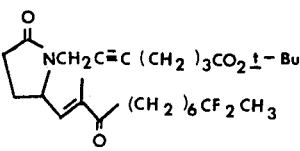 |
| 3. $(CH_3O)_2P(O)CH_2CO(CH_2)_4CH_3$ | h) | 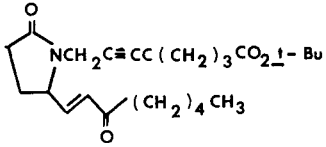 |
| 4. $(CH_3O)_2P(O)CH_2CO(CH_2)_8CF_3$ | i) | 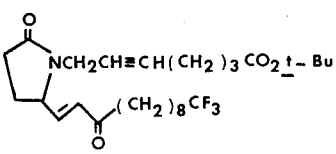 |
| c) 1. $(CH_3O)_2P(O)CH_2CO(CH_2)_4CH_3$ | j) | 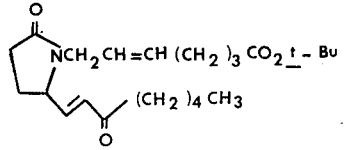 |

TABLE I-continued
c) 2. $(CH_3O)_2P(O)CH_2COC(CH_3)_2(CH_2)_3CH_3$     k) 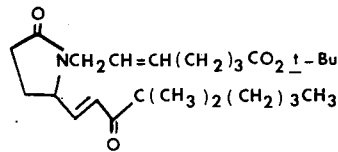
3. $(CH_3O)_2P(O)CH_2COC(CH_3)_2(CH_2)_3CF_3$     l) 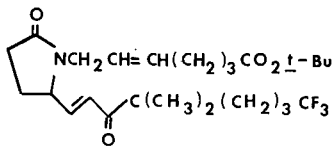
4. $(CH_3O)_2P(O)CH_2CO(CH_2)_3CF_2CH_3$     m) 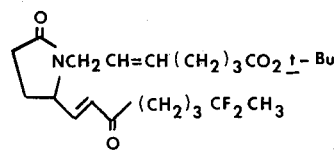
5. $(CH_3O)_2P(O)CH_2CO(CH_2)_8CF_3$     n) 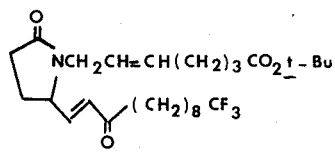
d) 1. $(CH_3O)_2P(O)CH_2CO(CH_2)_4CH_3$     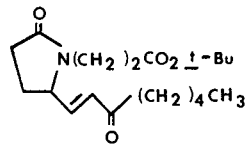
d) 2. $(CH_3O)_2P(O)CH_2COCH(C_2H_5)(CH_2)_2CF_3$     p) 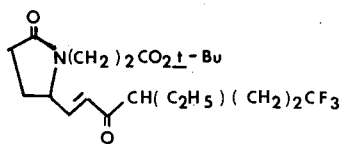
e) 1. $(CH_3O)_2P(O)CH(CH_3)CO(CH_2)_6CF_2CH_3$     q) 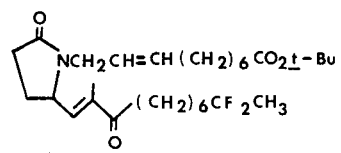
2. $(CH_3O)_2P(O)CH_2CO(CH_2)_4CF_3$     r) 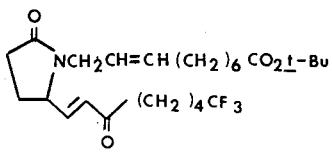

TABLE I-continued
f) 1. $(CH_3O)_2P(O)CH_2CO(CH_2)_4CH_3$     s) 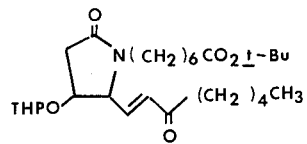
2. $(CH_3O)_2P(O)CH_2COC(CH_3)_2(CH_2)_3CH_3$     t) 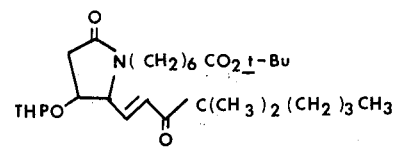
f) 3. $(CH_3O)_2P(O)CH_2COC(CH_3)_2(CH_2)_3CF_3$     u) 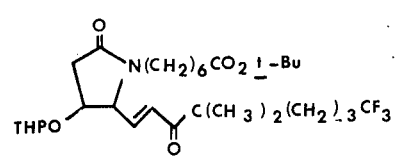
4. $(CH_3O)_2P(O)CH_2CO(CH_2)_4CF_3$     v) 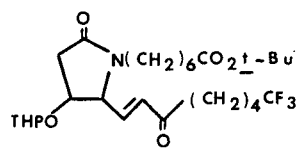
5. $(CH_3O)_2P(O)CH_2CO(CH_2)_3CF_2CH_3$     w) 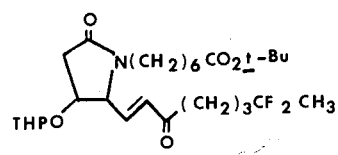
6. $(CH_3O)_2P(O)CH_2CO(CH_2)_8CH_3$     x) 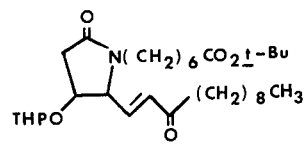
g) 1. $(CH_3O)_2P(O)CH_2CO(CH_2)_4CH_3$     y) 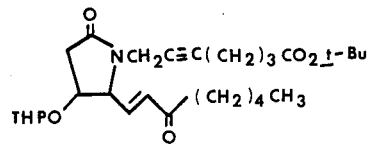
g) 2. $(CH_3O)_2P(O)CH_2COCH(C_2H_5)(CH_2)_3CF_3$     z) 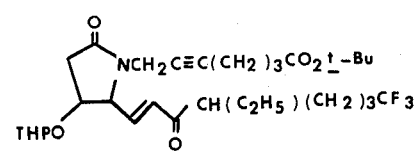
3. $(CH_3O)_2P(O)CH_2COC(CH_3)_2(CH_2)_4CH_3$     aa) 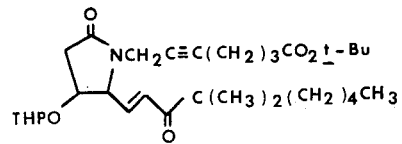

TABLE I-continued
| | | |
|---|---|---|
| 4. $(CH_3O)_2P(O)CH_2CO(CH_2)_3CF_2CH_3$ | bb) | 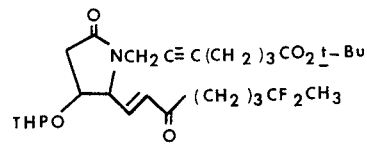 |
| h) 1. $(CH_3O)_2P(O)CH_2CO(CH_2)_4CH_3$ | cc) | 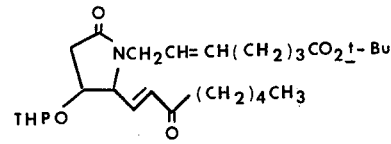 |
| 2. $(CH_3O)_2P(O)CH_2COC(CH_3)_2(CH_2)_3CH_3$ | dd) | 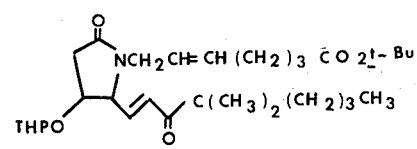 |
| h) 3. $(CH_3O)_2P(O)CH_2COC(CH_3)_2(CH_2)_3CF_3$ | ee) | 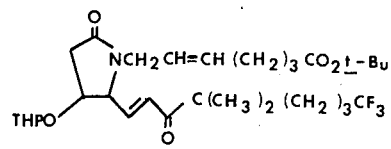 |
| 4. $(CH_3O)_2P(O)CH_2CO(CH_2)_4CF_3$ | ff) | 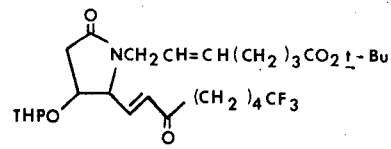 |
| 5. $(CH_3O)_2P(O)CH_2CO(CH_2)_3CF_2CH_3$ | gg) | 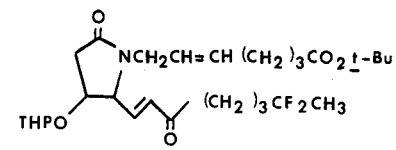 |
| 6. $(CH_3O)_2P(O)CH_2CO(CH_2)_8CH_3$ | hh) | 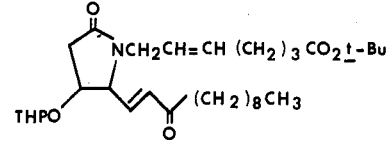 |
| i) 1. $(CH_3O)_2P(O)CH_2CO(CH_2)_8CF_3$ | ii) | 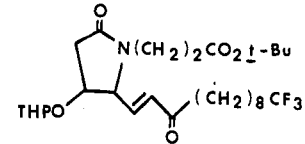 |

TABLE I-continued
i) 2. (CH₃O)₂P(O)CH₂COCH(C₂H₅)(CH₂)₂CF₃     jj) 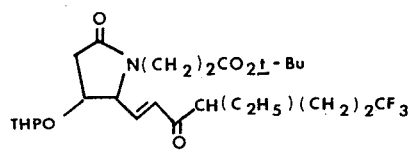
j) 1. (CH₃O)₂P(O)CH(CH₃)CO(CH₂)₂CF₂CH₃     kk) 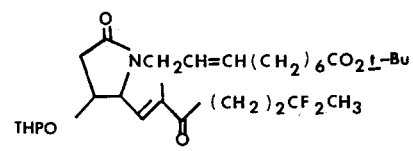
2. (CH₃O)₂P(O)CH₂CO(CH₂)₄CH₃     ll) 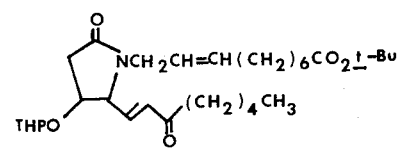
k) 1. (CH₃O)₂P(O)CH₂CO(CH₂)₄CH₃     mm) 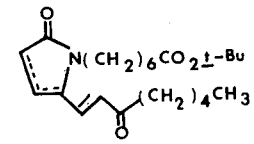
2. (CH₃O)₂P(O)CH₂COC(CH₃)₂(CH₂)₃CH₃     nn) 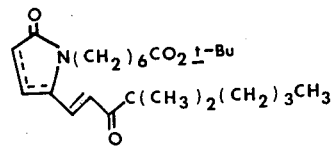
k) 3. (CH₃O)₂P(O)CH₂COC(CH₃)₂(CH₂)₃CF₃     oo) 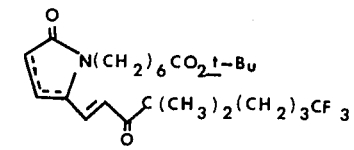
4. (CH₃O)₂P(O)CH₂CO(CH₂)₄CF₃     pp) 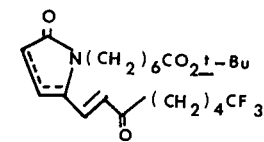
5. (CH₃O)₂P(O)CH₂CO(CH₂)₃CF₂CH₃     qq) 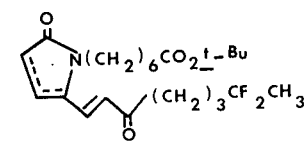

TABLE I-continued
| | | |
|---|---|---|
| 6. $(CH_3O)_2P(O)CH_2CO(CH_2)_8CH_3$ | rr) | 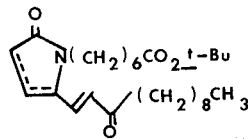 |
| l) 1. $(CH_3O)_2P(O)CH_2CO(CH_2)_4CH_3$ | ss) | 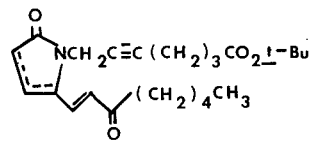 |
| 2. $(CH_3O)_2P(O)CH_2COCH(C_2H_5)(CH_2)_3CF_3$ | tt) | 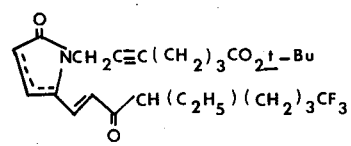 |
| l) 3. $(CH_3O)_2P(O)CH_2COC(CH_3)_2(CH_2)_4CH_3$ | uu) | 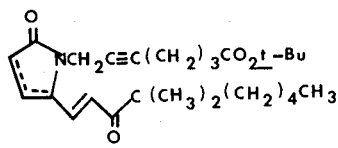 |
| 4. $(CH_3O)_2P(O)CH_2CO(CH_2)_3CF_2CH_3$ | vv) | 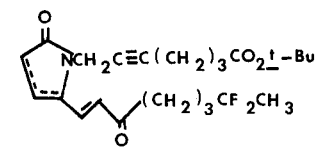 |
| m) 1. $(CH_3O)_2P(O)CH_2CO(CH_2)_4CH_3$ | ww) | 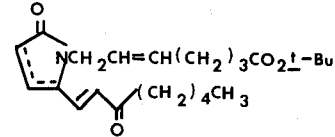 |
| 2. $(CH_3O)_2P(O)CH_2COC(CH_3)_2(CH_2)_3CH_3$ | xx) | 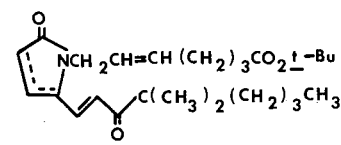 |
| 3. $(CH_3O)_2P(O)CH_2COC(CH_3)_2(CH_2)_3CF_3$ | yy) | 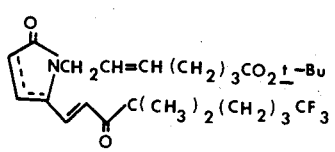 |
| 4. $(CH_3O)_2P(O)CH_2CO(CH_2)_4CF_3$ | zz) | 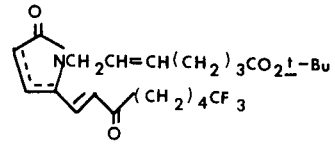 |

TABLE I-continued
| | | |
|---|---|---|
| m) 5. $(CH_3O)_2P(O)CH_2CO(CH_2)_3CF_2CH_3$ | aaa) | 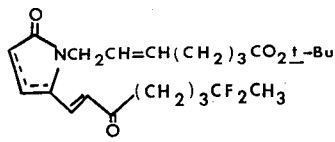 |
| 6. $(CH_3O)_2P(O)CH_2CO(CH_2)_8CH_3$ | bbb) | 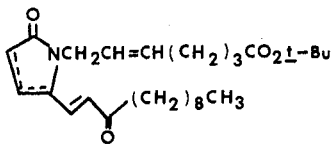 |
| n) 1. $(CH_3O)_2P(O)CH_2CO(CH_2)_8CF_3$ | ccc) | 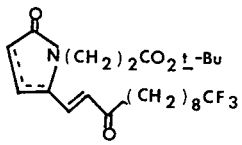 |
| 2. $(CH_3O)_2P(O)CH_2COCH(C_2H_5)(CH_2)_2CF_3$ | ddd) | 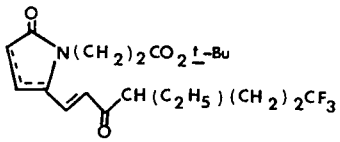 |
| o) 1. $(CH_3O)_2P(O)CH(CH_3)CO(CH_2)_2CF_2CH_3$ | eee) | 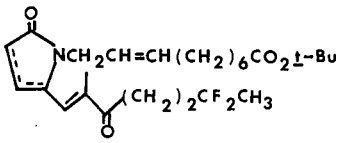 |
| 2. $(CH_3O)_2P(O)CH_2CO(CH_2)_4CH_3$ | fff) | 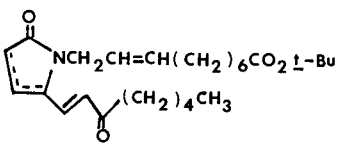 |
| p) 1. $(CH_3O)_2P(O)CH_2CO(CH_2)_4CH_3$ | (g³) | 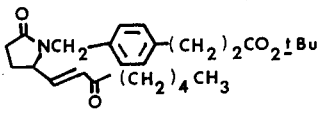 |
| 2. $(CH_3O)_2P(O)CH_2COC(CH_3)_2(CH_2)_3CH_3$ | (h³) | 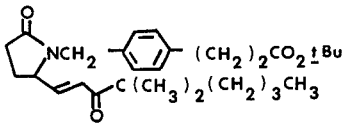 |
| 3. $(CH_3O)_2P(O)CH_2CO(CH_2)_4CF_3$ | (i³) | 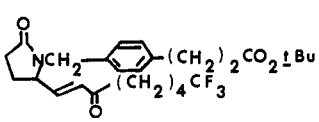 |

TABLE I-continued

| | | |
|---|---|---|
| 4. $(CH_3O)_2P(O)CH_2CO(CH_2)_3CF_2CH_3$ | ($j^3$) | [pyrrolidinone with $NCH_2$-C$_6$H$_4$-$(CH_2)_2CO_2tBu$ and enone $(CH_2)_3CF_2CH_3$] |
| 5. $(CH_3O)_2P(O)CH_2CO(CH_2)_8CH_3$ | ($k^3$) | [pyrrolidinone with $NCH_2$-C$_6$H$_4$-$(CH_2)_2CO_2tBu$ and enone $(CH_2)_8CH_3$] |
| q) 1. $(CH_3O)_2P(O)CH_2CO(CH_2)_4CH_3$ | ($l^3$) | [THPO-pyrrolidinone with $NCH_2$-C$_6$H$_4$-$(CH_2)_2CO_2tBu$ and enone $(CH_2)_4CH_3$] |
| 2. $(CH_3O)_2P(O)CH_2COC(CH_3)_2(CH_2)_3CH_3$ | ($m^3$) | [THPO-pyrrolidinone with $NCH_2$-C$_6$H$_4$-$(CH_2)_2CO_2tBu$ and enone $C(CH_3)_2(CH_2)_3CH_3$] |
| 3. $(CH_3O)_2P(O)CH_2COC(CH_3)_2(CH_2)_3CF_3$ | $n^3$) | [THPO-pyrrolidinone with $NCH_2$-C$_6$H$_4$-$(CH_2)_2CO_2tBu$ and enone $C(CH_3)_2(CH_2)_3CF_3$] |
| 4. $(CH_3O)_2P(O)CH_2CO(CH_2)_4CF_3$ | $o^3$) | [THPO-pyrrolidinone with $NCH_2$-C$_6$H$_4$-$(CH_2)_2CO_2tBu$ and enone $(CH_2)_4CF_3$] |
| 5. $(CH_3O)_2P(O)CH_2CO(CH_2)_3CF_2CH_3$ | $p^3$) | [THPO-pyrrolidinone with $NCH_2$-C$_6$H$_4$-$(CH_2)_2CO_2tBu$ and enone $(CH_2)_3CF_2CH_3$] |
| 6. $(CH_3O)_2P(O)CH_2CO(CH_2)_8CH_3$ | $q^3$) | [THPO-pyrrolidinone with $NCH_2$-C$_6$H$_4$-$(CH_2)_2CO_2tBu$ and enone $(CH_2)_8CH_3$] |
| r) 1. $(CH_3O)_2P(O)CH_2CO(CH_2)_4CH_3$ | $r^3$) | [pyrrolinone with $NCH_2$-C$_6$H$_4$-$(CH_2)_2CO_2tBu$ and enone $(CH_2)_4CH_3$] |
| 2. $(CH_3O)_2 1. 2COC(CH_3)_2(CH_2)_3CH_3$ | $s^3$) | [pyrrolinone with $NCH_2$-C$_6$H$_4$-$(CH_2)_2CO_2tBu$ and enone $C(CH_3)_2(CH_2)_3CH_3$] |
| 3. $(CH_3O)_2P(O)CH_2CO(CH_2)_4CF_3$ | $t^3$) | [pyrrolinone with $NCH_2$-C$_6$H$_4$-$(CH_2)_2CO_2tBu$ and enone $(CH_2)_4CF_3$] |
| 4. $(CH_3O)_2P(O)CH_2CO(CH_2)_3CF_2CH_3$ | $u^3$) | [pyrrolinone with $NCH_2$-C$_6$H$_4$-$(CH_2)_2CO_2tBu$ and enone $(CH_2)_3CF_2CH_3$] |

TABLE I-continued
| | | |
|---|---|---|
| 5. $(CH_3O)_2P(O)CH_2CO(CH_2)_nCH_3$ | v³) | 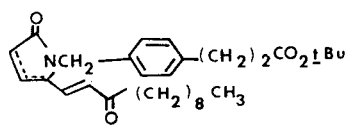 |
| G | | H | |
|---|---|---|---|
| a) 1. $Zn(BH_4)_2$ | | a) | 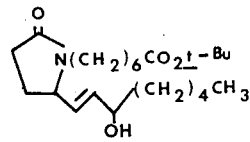 |
| 2. $CH_3MgBr$ | | b) | 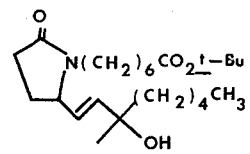 |
| b) 1. $Zn(BH_4)_2$ | | c) | 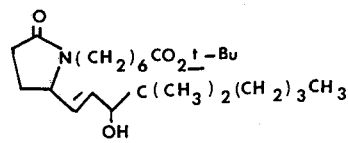 |
| 2. Na/THF/t-BuOH; $NaBH_4$ | | d) | 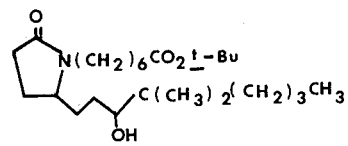 |
| c) 1. $Zn(BH_4)_2$ | | e) | 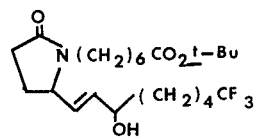 |
| 2. $CH_3CH_2MgBr$ | | f) | 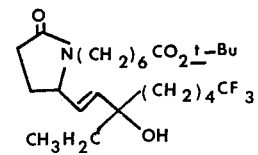 |
| c) 3. Na/THF/t-BuOH; $CH_2=CHMgBr$ | | g) | 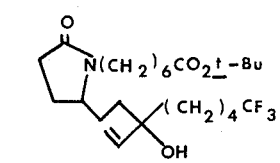 |

TABLE I-continued
d) 1. Zn(BH₄)₂   h) 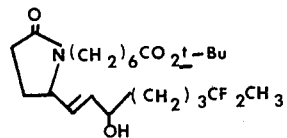
2. CH₃MgBr   i) 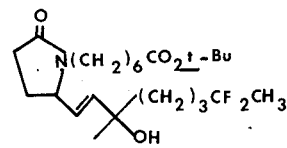
e) 1. Zn(BH₄)₂   j) 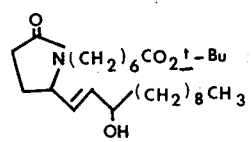
2. Na/THF/t-BuOH; HC≡C⁻Li⁺   k) 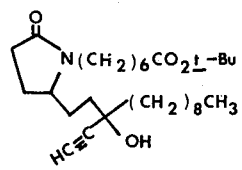
f) 1. Zn(BH₄)₂   l) 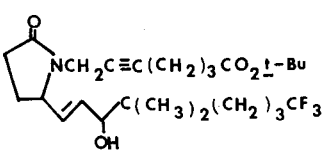
g) 1. Zn(BH₄)₂   m) 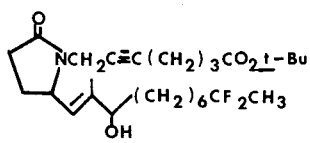
2. CH₂CH₂MgBr   n) 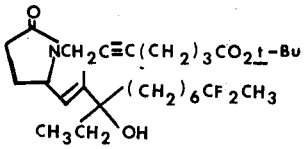
h) 1. Zn(BH₄)₂   o) 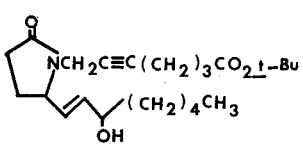
2. CH₃MgBr   p) 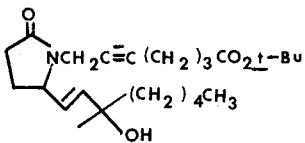

TABLE I-continued
| | | | |
|---|---|---|---|
| i) | 1. Zn(BH$_4$)$_2$ | q) | 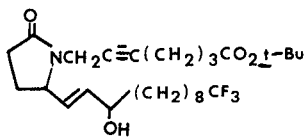 |
| j) | 1. Zn(BH$_4$)$_2$ | r) | 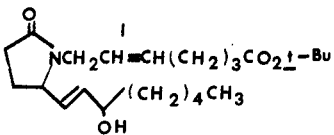 |
| j) | 2. CH$_3$MgBr | s) | 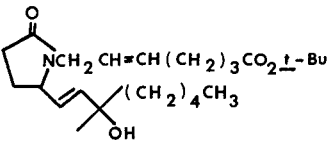 |
| | 3. Na/THF/t-BuOH; CH$_2$=CHMgBr | t) | 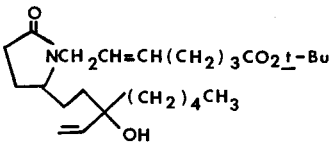 |
| k) | 1. Zn(BH$_4$)$_2$ | u) | 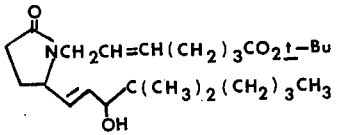 |
| l) | 1. Zn(BH$_4$)$_2$ | v) | 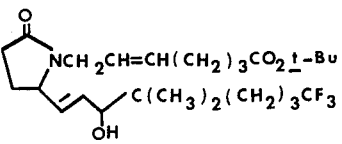 |
| | 2. Na/THF/t-BuOH; NaBH$_4$ | w) | 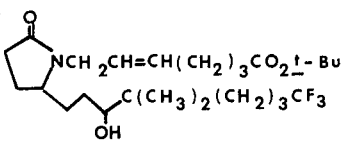 |
| m) | 1. Zn(BH$_4$)$_2$ | x) | 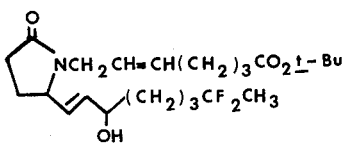 |

TABLE I-continued
| | | | |
|---|---|---|---|
| m) 2. CH₃MgBr | | y) | 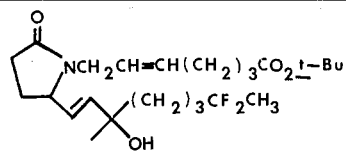 |
| n) 1. Zn(BH₄)₂ | | z) | 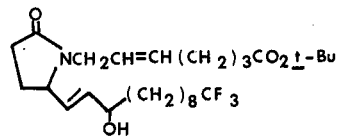 |
| 2. (n)C₄H₉MgBr | | aa) | 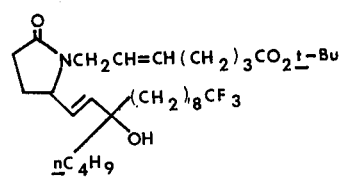 |
| o) 1. Zn(BH₄)₂ | | bb) | 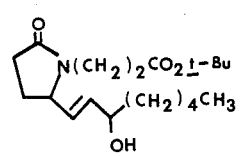 |
| 2. HC≡C⁻Li⁺ | | cc) | 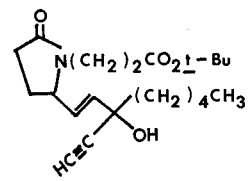 |
| p) 1. Zn(BH₄)₂ | | dd) | 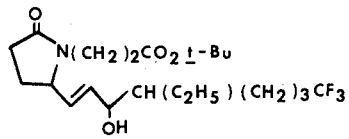 |
| q) 1. Zn(BH₄)₂ | | ee) | 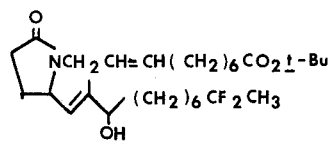 |
| r) 1. Zn(BH₄)₂ | | ff) | 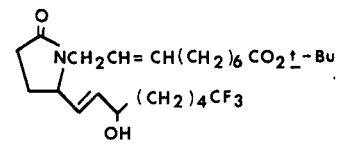 |
| 2. nC₃H₇MgBr | | gg) | 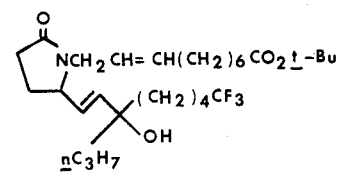 |

TABLE I-continued

| | | |
|---|---|---|
| s) 1. Zn(BH$_4$)$_2$ | hh) | 5-[CH=CH-CH(OH)-(CH$_2$)$_4$CH$_3$]-4-THPO-1-[(CH$_2$)$_6$CO$_2$-t-Bu]-pyrrolidin-2-one |
| 2. CH$_3$MgBr | ii) | 5-[CH=CH-C(CH$_3$)(OH)-(CH$_2$)$_4$CH$_3$]-4-THPO-1-[(CH$_2$)$_6$CO$_2$-t-Bu]-pyrrolidin-2-one |
| t) 1. Zn(BH$_4$)$_2$ | jj) | 5-[CH=CH-CH(OH)-C(CH$_3$)$_2$(CH$_2$)$_3$CH$_3$]-4-THPO-1-[(CH$_2$)$_6$CO$_2$-t-Bu]-pyrrolidin-2-one |
| u) 1. Zn(BH$_4$)$_2$ | kk) | 5-[CH=CH-CH(OH)-C(CH$_3$)$_2$(CH$_2$)$_3$CF$_3$]-4-THPO-1-[(CH$_2$)$_6$CO$_2$-t-Bu]-pyrrolidin-2-one |
| v) 1. Zn(BH$_4$)$_2$ | ll) | 5-[CH=CH-CH(OH)-(CH$_2$)$_4$CF$_3$]-4-THPO-1-[(CH$_2$)$_6$CO$_2$-t-Bu]-pyrrolidin-2-one |
| 2. CH$_3$MgBr | mm) | 5-[CH=CH-C(CH$_3$)(OH)-(CH$_2$)$_4$CF$_3$]-4-THPO-1-[(CH$_2$)$_6$CO$_2$-t-Bu]-pyrrolidin-2-one |
| 3. Na/THF/t-BuOH; CH$_2$=CHMgBr | nn) | 5-[CH$_2$-C(CH=CH$_2$)(OH)-(CH$_2$)$_4$CF$_3$]-4-THPO-1-[(CH$_2$)$_6$CO$_2$-t-Bu]-pyrrolidin-2-one |
| w) 1. Zn(BH$_4$)$_2$ | oo) | 5-[CH=CH-CH(OH)-(CH$_2$)$_3$CF$_2$CH$_3$]-4-THPO-1-[(CH$_2$)$_6$CO$_2$-t-Bu]-pyrrolidin-2-one |

TABLE I-continued
| | | |
|---|---|---|
| w 2. C₂H₅MgBr | pp) | 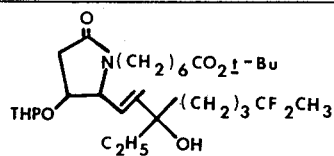 |
| x) 1. Zn(BH₄)₂ | qq) | 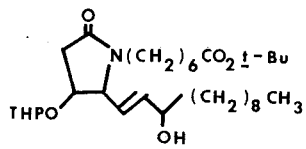 |
| y) 1. Zn(BH₄)₂ | rr) | |
| 2. C₂H₅MgBr | ss) | 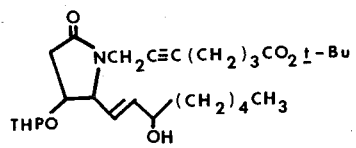 |
| z) 1. Zn(BH₄)₂ | tt) | 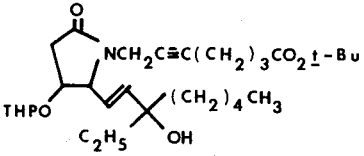 |
| aa) 1. Zn(BH₄)₂ | uu) | 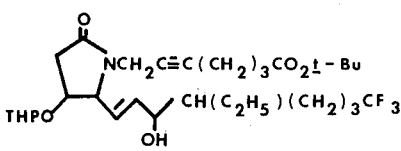 |
| bb) 1. Zn(BH₄)₂ | vv) | 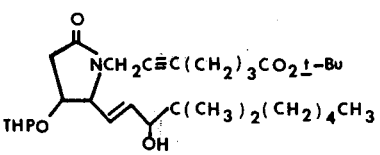 |
| 2. CH₃MgBr | ww) | 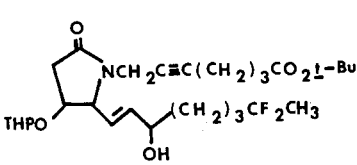 |
| cc) 1. Zn(BH₄)₂ | xx) | 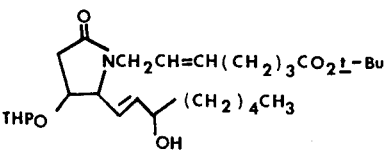 |

TABLE I-continued
| | | | |
|---|---|---|---|
| | 2. CH₃MgBr | yy) | |
| cc) 3. Na/THF/t-BuOH; HC≡C⁻Li⁺ | | zz) | |
| dd) 1. Zn(BH₄)₂ | | aaa) | |
| ee) 1. Zn(BH₄)₂ | | bbb) | |
| ff) 1. Zn(BH₄)₂ | | ccc) | |
| | 2. C₂H₅MgBr | ddd) | |
| gg) 1. Zn(BH₄)₂ | | eee) | |
| gg) 2. CH₃MgBr | | fff) | |
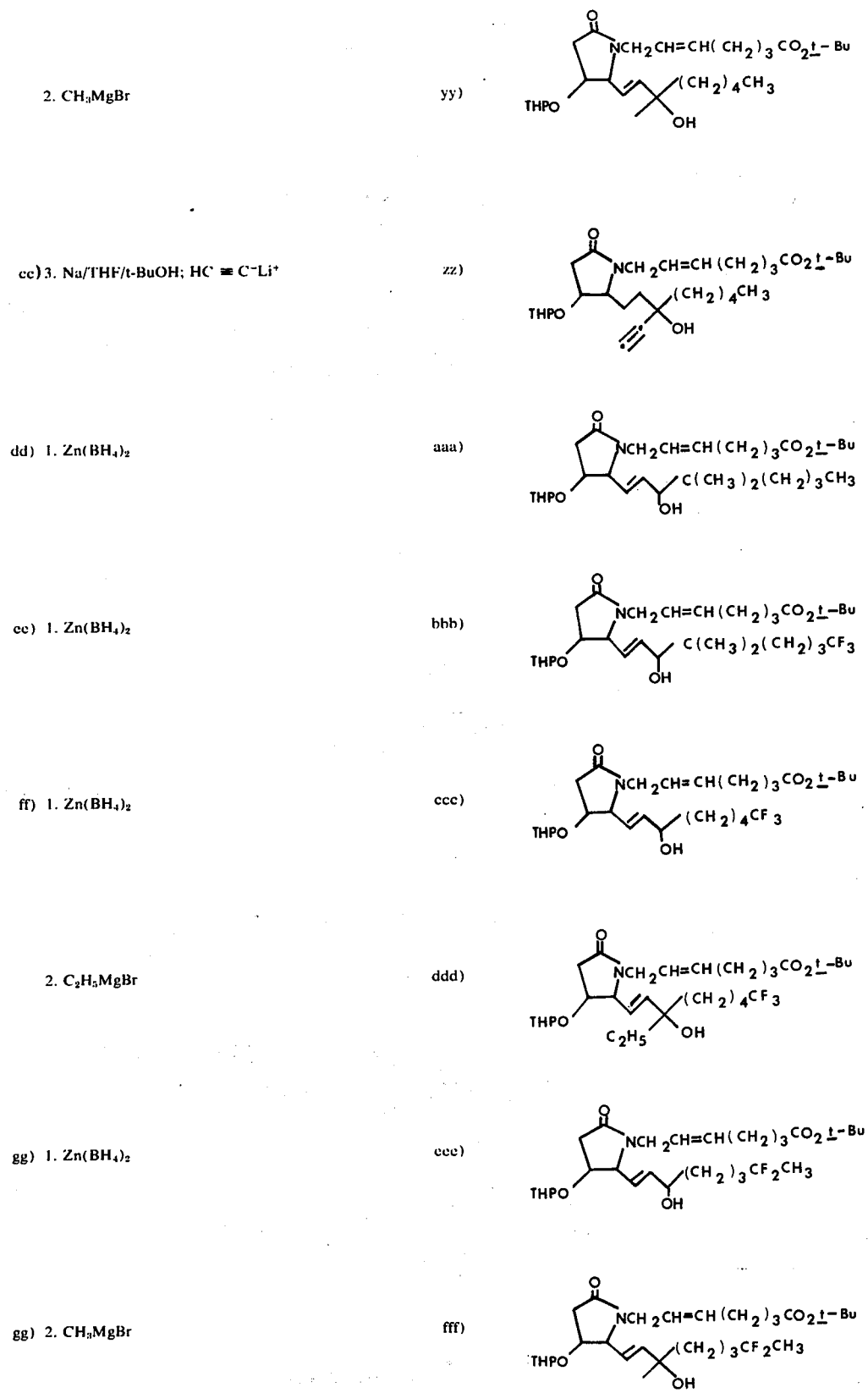

TABLE I-continued
| | | | |
|---|---|---|---|
| hh) | 1. Na/THF/t-BuOH; CH₂=CHMgBr | ggg) | 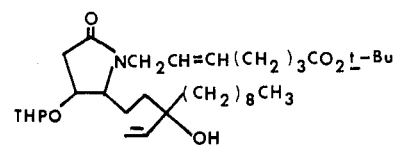 |
| ii) | 1. Zn(BH₄)₂ | hhh) | 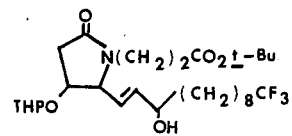 |
| | 2. nC₄H₉MgBr | iii) | 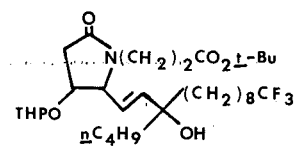 |
| jj) | 1. Zn(BH₄)₂ | jjj) | 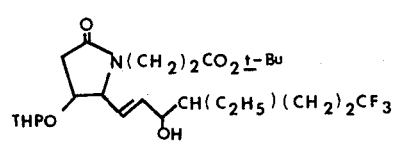 |
| kk) | 1. Zn(BH₄)₂ | kkk) | 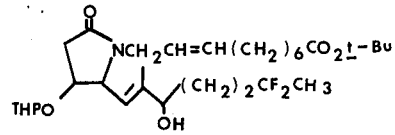 |
| ll) | 1. Zn(BH₄)₂ | lll) | 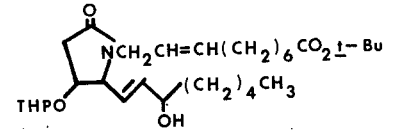 |
| | 2. Na/THF/t-BuOH; C₂H₅MgBr | mmm) | 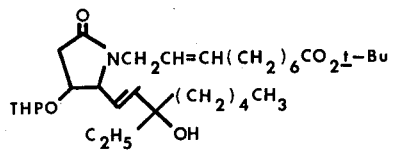 |
| mm) | 1. Zn(BH₄)₂ | nnn) | 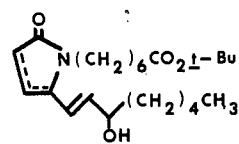 |
| | 2. CH₃MgBr | ooo) | 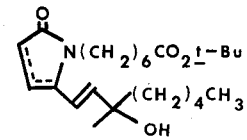 |

TABLE I-continued
| | | | |
|---|---|---|---|
| nn) 1. Zn(BH₄)₂ | | ppp) | 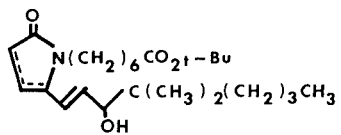 |
| oo) 1. CH₃MgBr | | qqq) | 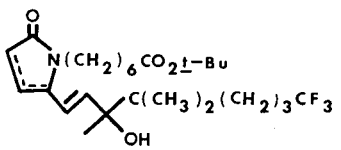 |
| pp) 1. Zn(BH₄)₂ | | rrr) | 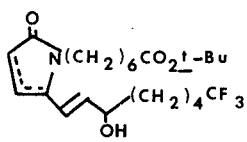 |
| 2. C₂H₅MgBr | | sss) | 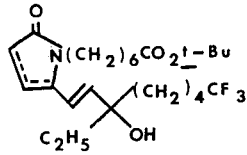 |
| qq) 1. Zn(BH₄)₂ | | ttt) | 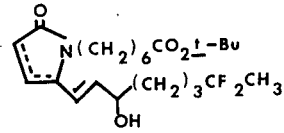 |
| 2. CH₃MgBr | | uuu) | 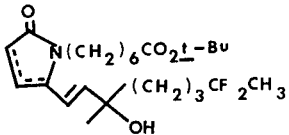 |
| rr) 1. Zn(BH₄)₂ | | vvv) | 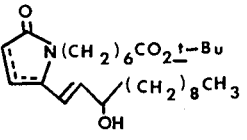 |
| 2. nC₄H₉MgBr | | www) | 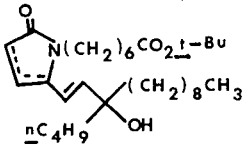 |

TABLE I-continued
| | | | |
|---|---|---|---|
| ss) 1. Zn(BH₄)₂ | xxx) | 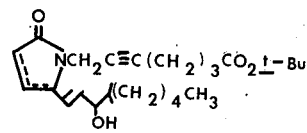 | |
| 2. CH₃MgBr | yyy) | 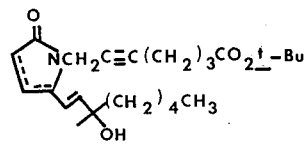 | |
| tt) 1. Zn(BH₄)₂ | zzz) | 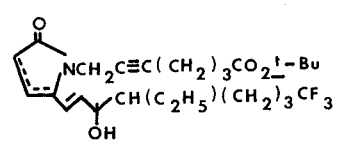 | |
| uu) 1. Zn(BH₄)₂ | a⁴) | 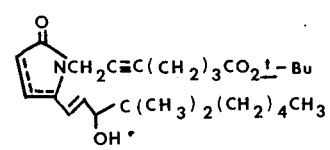 | |
| vv) 1. Zn(BH₄)₂ | b⁴) | 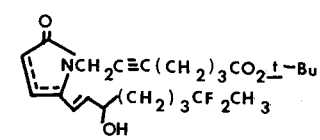 | |
| 2. C₂H₅MgBr | c⁴) | 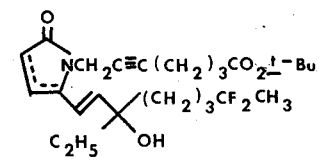 | |
| ww) 1. Zn(BH₄)₂ | d⁴) | 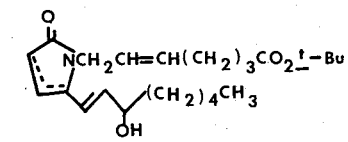 | |
| 2. CH₃MgBr | e⁴) | 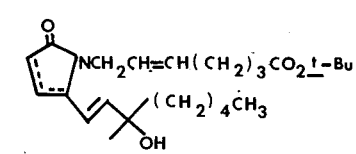 | |

TABLE I-continued xx) 1. Zn(BH$_4$)$_2$     f$^4$)

Structure: pyrrolinone with N-CH$_2$CH=CH(CH$_2$)$_3$CO$_2$t-Bu; side chain -CH=CH-CH(OH)-C(CH$_3$)$_2$(CH$_2$)$_3$CH$_3$ yy) 1. Zn(BH$_4$)$_2$     g$^4$)

Structure: pyrrolinone with N-CH$_2$CH=CH(CH$_2$)$_3$CO$_2$t-Bu; side chain -CH=CH-CH(OH)-C(CH$_3$)$_2$(CH$_2$)$_3$CF$_3$ zz) 1. Zn(BH$_4$)$_2$     h$^4$)

Structure: pyrrolinone with N-CH$_2$CH=CH(CH$_2$)$_3$CO$_2$t-Bu; side chain -CH=CH-CH(OH)-(CH$_2$)$_4$CF$_3$ 2. CH$_3$MgBr     i$^4$)

Structure: pyrrolinone with N-CH$_2$CH=CH(CH$_2$)$_3$CO$_2$t-Bu; side chain -CH=CH-C(CH$_3$)(OH)-(CH$_2$)$_4$CF$_3$ aaa) 1. Zn(BH$_4$)$_2$     j$^4$)

Structure: pyrrolinone with N-CH$_2$CH=CH(CH$_2$)$_3$CO$_2$t-Bu; side chain -CH=CH-CH(OH)-(CH$_2$)$_3$CF$_2$CH$_3$ 2. C$_2$H$_5$MgBr     k$^4$)

Structure: pyrrolinone with N-CH$_2$CH=CH(CH$_2$)$_3$CO$_2$t-Bu; side chain -CH=CH-C(C$_2$H$_5$)(OH)-(CH$_2$)$_3$CF$_2$CH$_3$ bbb) 1. Zn(BH$_4$)$_2$     l$^4$)

Structure: pyrrolinone with N-CH$_2$CH=CH(CH$_2$)$_3$CO$_2$t-Bu; side chain -CH=CH-CH(OH)-(CH$_2$)$_8$CF$_3$ ccc) 1. Zn(BH$_4$)$_2$     m$^4$)

Structure: pyrrolinone with N-(CH$_2$)$_2$CO$_2$t-Bu; side chain -CH=CH-CH(OH)-(CH$_2$)$_8$CF$_3$ 2. CH$_3$MgBr     n$^4$)

Structure: pyrrolinone with N-(CH$_2$)$_2$CO$_2$t-Bu; side chain -CH=CH-C(CH$_3$)(OH)-(CH$_2$)$_8$CF$_3$

TABLE I-continued
| | | | |
|---|---|---|---|
| ddd) | 1. Zn(BH₄)₂ | o⁴) | 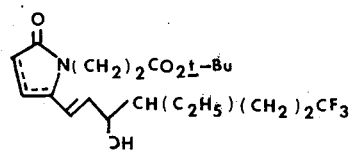 |
| eee) | 1. Zn(BH₄)₂ | p⁴) | 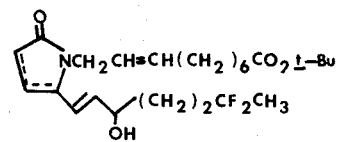 |
| fff) | 1. Zn(BH₄)₂ | q⁴) | 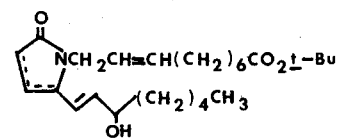 |
| | 2. nC₃H₇MgBr | r⁴) | 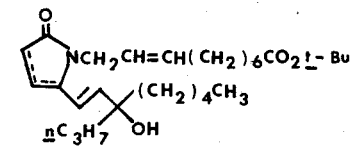 |
| g³) | 1. Zn(BH₄)₂ | s⁴) | 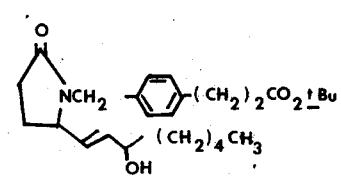 |
| ) | 2. CH₃MgBr | t⁴) | 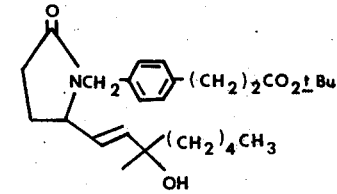 |
| h³) | 1. Zn(BH₄)₂ | u⁴) | 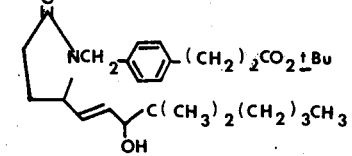 |
| ) | 2. CH₃MgBr | v⁴) | 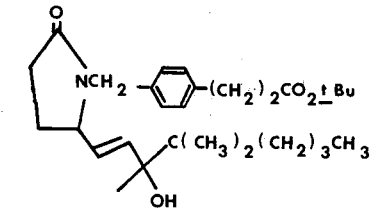 |

TABLE 1-continued
n³) Zn(BH₄)₂    f⁵)    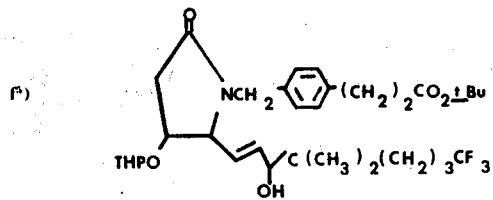
o³) 1. Zn(BH₄)₂    g⁵)    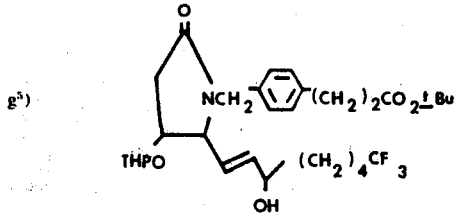
) 2. CH₃CH₂MgBr    h⁵)    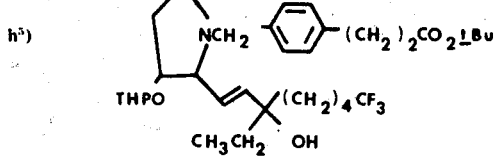
p³) 1. Zn(BH₄)₂    i⁵)    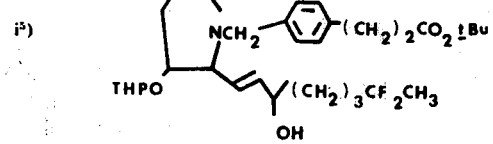
) 2. CH₃MgBr    j⁵)    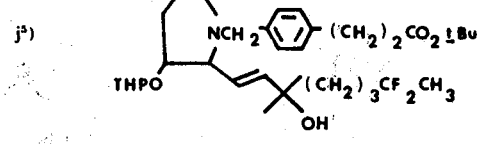
q³) 1. Zn(BH₄)₂    k⁵)    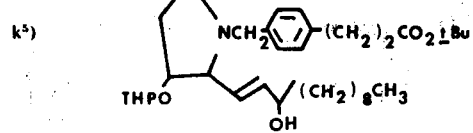
) 2. CH₃MgBr    l⁵)    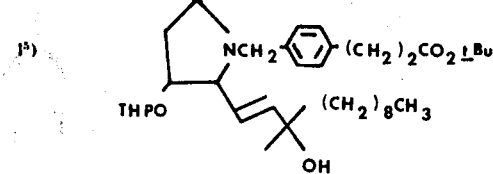

TABLE I-continued
| | | | |
|---|---|---|---|
| r³) 1. Zn(BH₄)₂ | | m⁵) | 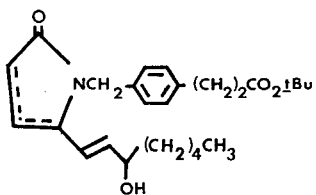 |
| ) 2. CH₃MgBr | | n⁵) | 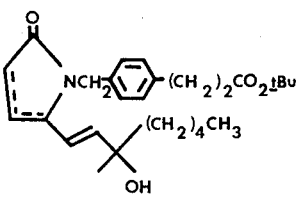 |
| s³) Zn(BH₄)₂ | | o⁵) | 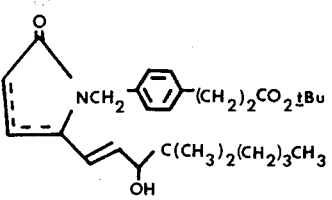 |
| t³) 1. Zn(BH₄)₂ | | p⁵) | 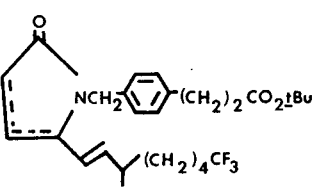 |
| ) 2. CH₃MgBr | | q⁵) | 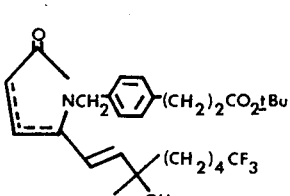 |
| u³) 1. Zn(BH₄)₂ | | r⁵) | 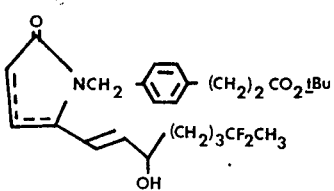 |
| ) 2. CH₃CH₂MgBr | | s⁵) | 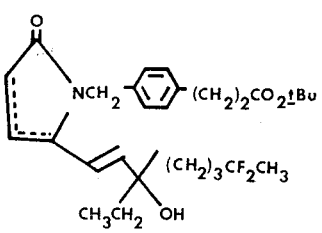 |

TABLE I-continued
| | I | | J |
|---|---|---|---|
| v³) | Zn(BH₄)₂ | t⁵) | 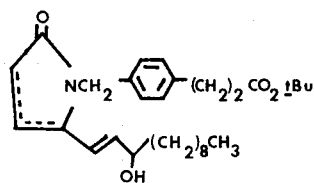 |
| a) | — | a) | 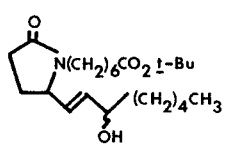 |
| b) | C₂H₅I, NaH | b) | 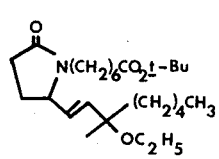 |
| c) | CH₃I, NaH | c) | 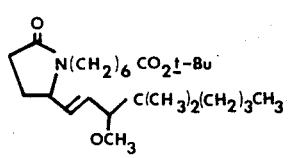 |
| d) | PhCH₂I, NaH | d) | 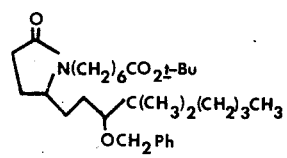 |
| e) | CH₃COCl, (C₂H₅)₃N | e) | 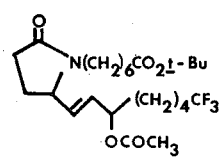 |
| f | — | f) | 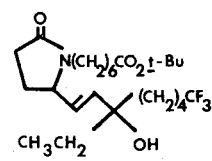 |

TABLE I-continued
| | | | |
|---|---|---|---|
| g) CH₃I, NaH | | g) | 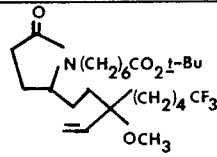 |
| h) — | | h) | 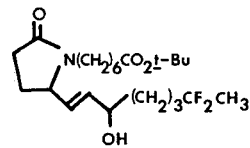 |
| i) CH₃I, NaH | | i) | 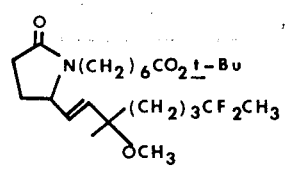 |
| j) — | | j) | 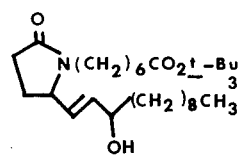 |
| k) PhCH₂I, NaH | | k) | 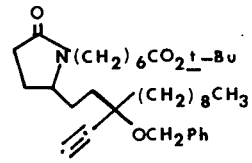 |
| l) CH₃COCl, (C₂H₅)₃N | | l) | 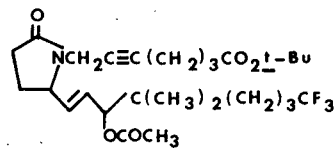 |
| m) — | | m) | 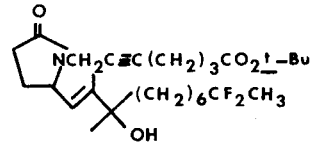 |
| n) C₂H₅I, NaH | | n) | 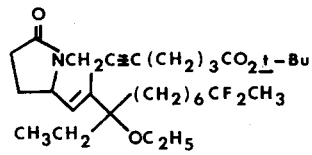 |
| o) — | | o) | 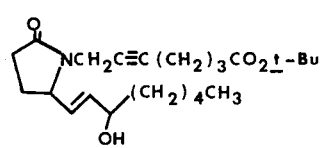 |

TABLE I-continued
p) CH₃I, NaH      p) 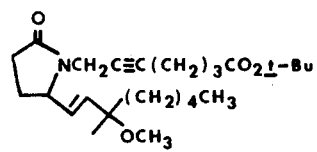
q) —              q) 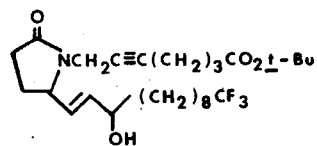
r) —              r) 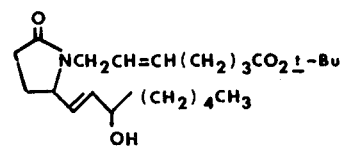
s) CH₃COCl, (C₂H₅)₃N    s) 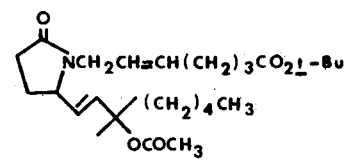
t) C₂H₅I, NaH     t) 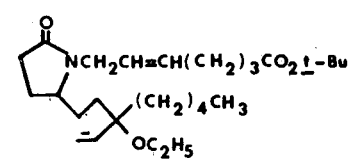
u) —              u) 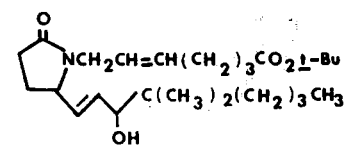
v) —              v) 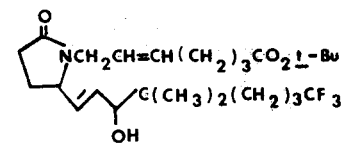
w) PhCH₂I, NaH    w) 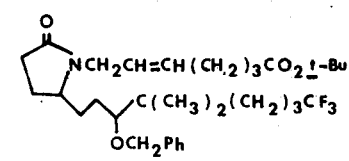

TABLE I-continued
| | | | |
|---|---|---|---|
| x) | — | x) | 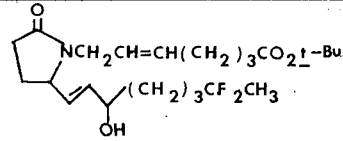 |
| y) | CH₃I, NaH | y) | 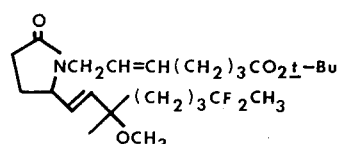 |
| z) | CH₃COCl, (C₂H₅)₃N | z) | 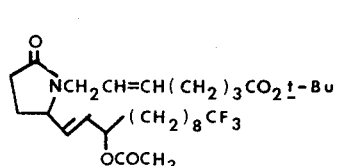 |
| a²) | C₂H₅I, NaH | a²) | 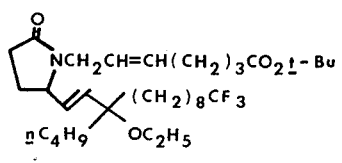 |
| b²) | PhCH₂I, NaH | b²) | 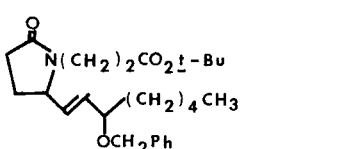 |
| c²) | CH₃I, NaH | c²) | 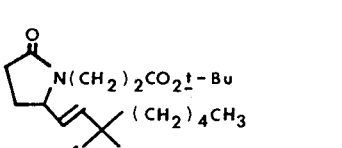 |
| d²) | PhCH₂I, NaH | d²) | 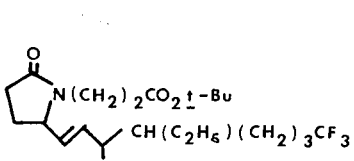 |
| e²) | CH₃COCl, (C₂H₅)₃N | e²) | 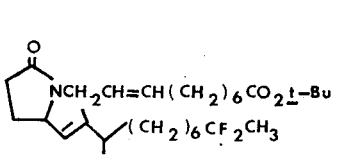 |
| f²) | — | f²) | 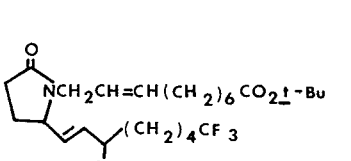 |

TABLE I-continued
g²) C₂H₅I, NaH
g²) 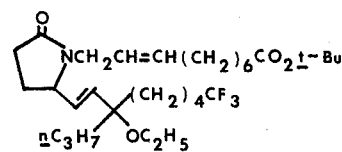
h²) —
h²) 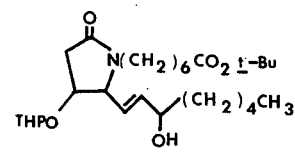
i²) CH₃COCl, (C₂H₅)₃N
i²) 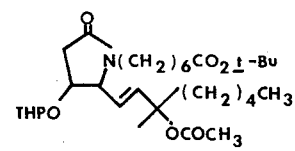
j²) —
j²) 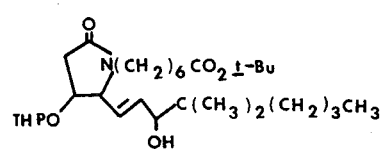
k²) CH₃I, NaH
k²) 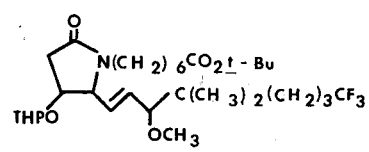
l²) —
l²) 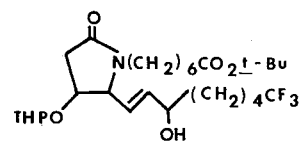
m²) C₂H₅I, NaH
m²) 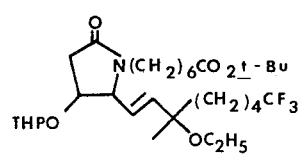
n²) CH₃COCl, (C₂H₅)₃N
n²) 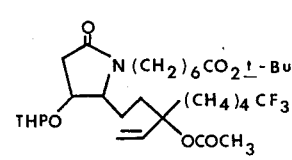

TABLE I-continued
| | | | |
|---|---|---|---|
| o²) | — | o²) | 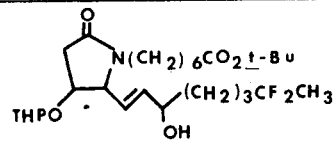 |
| p²) | CH₃I, NaH | p²) | 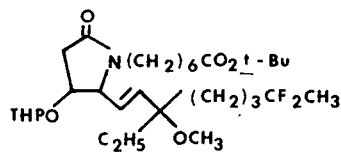 |
| q²) | CH₃COCl, (C₂H₅)₃N | q²) | 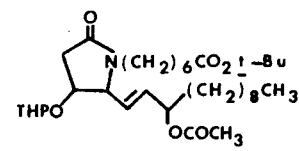 |
| r²) | CH₃I, NaH | r²) | 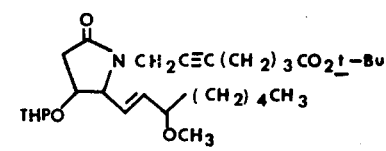 |
| s²) | PhCH₂I, NaH | s²) | 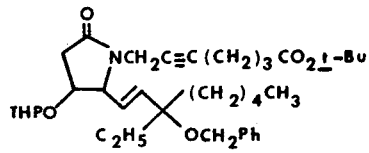 |
| t²) | — | t²) | 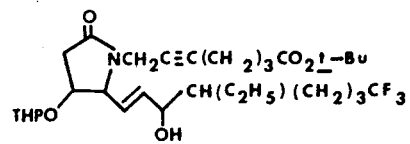 |
| u²) | — | u²) | 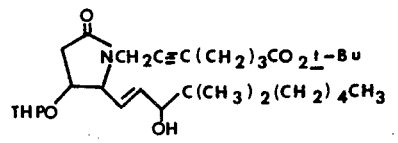 |
| v²) | C₂H₅I, NaH | v²) | 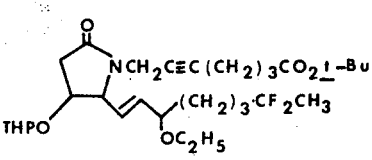 |
| w²) | CH₃I, NaH | w²) | 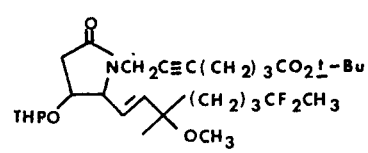 |

TABLE I-continued
x²) —    x²) 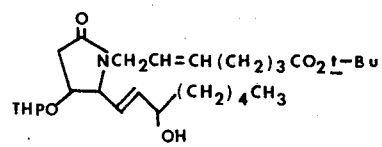
y²) CH₃COCl, (C₂H₅)₃N    y²) 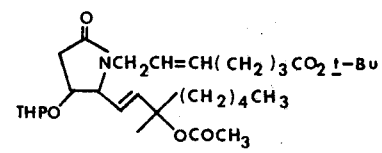
z²) CH₃I, NaH    z²) 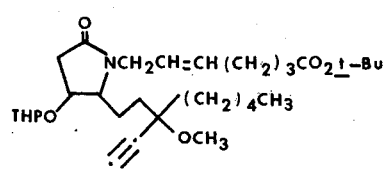
a³) —    a³) 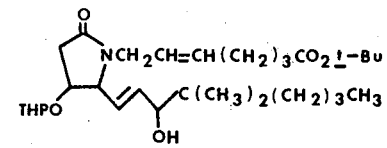
b³) C₂H₅I, NaH    b³) 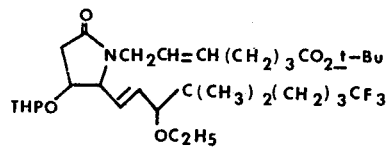
c³) CH₃I, NaH    c³) 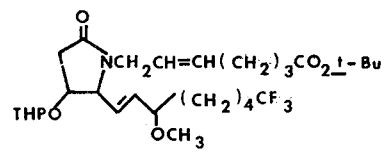
d³) CH₃COCl, (C₂H₅)₃N    d³) 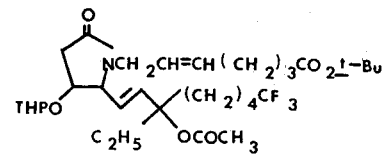
e³) —    e³) 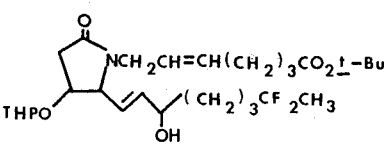

TABLE I-continued
| | | | |
|---|---|---|---|
| f³) CH₃I, NaH | | f³) | 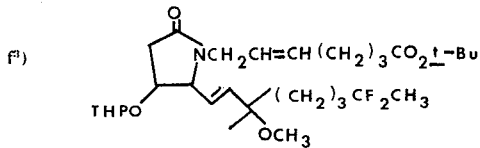 |
| g³) C₂H₅COCl, (C₂H₅)₃N | | g³) | 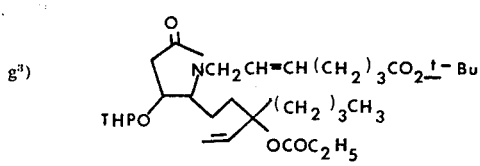 |
| h³) C₂H₅I, NaH | | h³) | 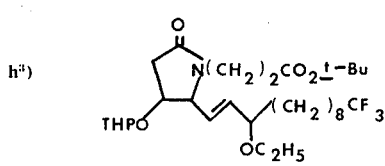 |
| i³) CH₃I, NaH | | i³) | 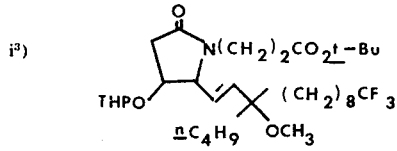 |
| j³) — | | j³) | 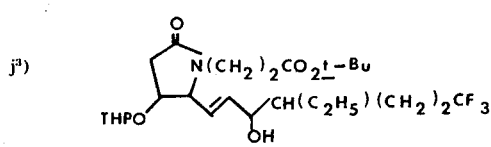 |
| k³) CH₃COCl, (C₂H₅)₃N | | k³) | 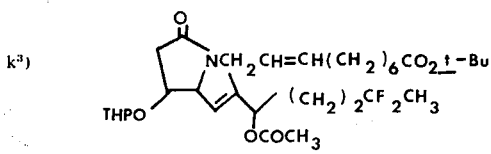 |
| l³) — | | l³) | 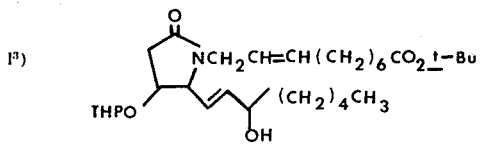 |
| m³) CH₃I, NaH | | m³) | 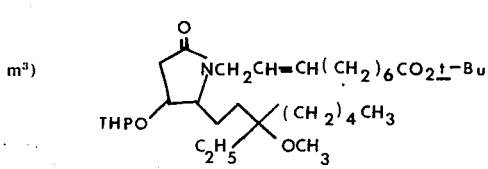 |
| n³) — | | n³) | 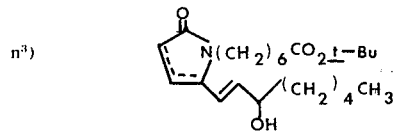 |

TABLE I-continued
o³) (CH₃)₂CHCOCl, (C₂H₅)₃N    o³) 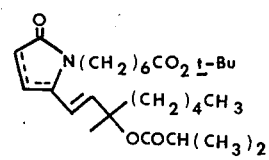
p³) —    p³) 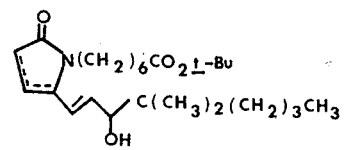
q³) CH₃COCl, (C₂H₅)₃N    q³) 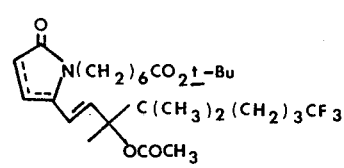
r³) —    r³) 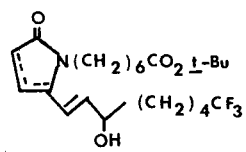
s³) CH₃I, NaH    s³) 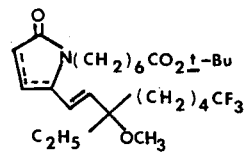
t³) —    t³) 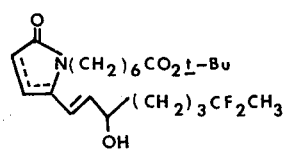
u³) C₂H₅COCl, (C₂H₅)₃N    u³) 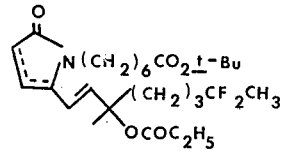
v³) C₂H₅I, NaH    v³) 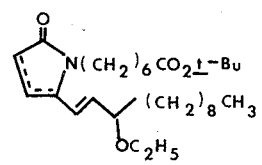

TABLE I-continued
w³) CH₃COCl, (C₂H₅)₃N
w³) 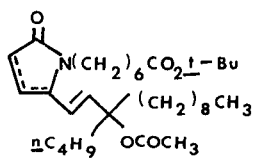
x³) —
x³) 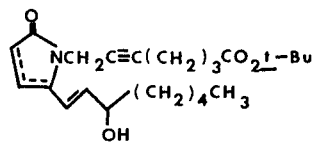
y³) CH₃I, NaH
y³) 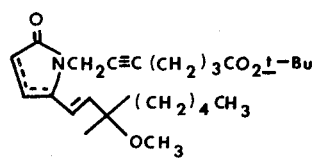
z³) nC₃H₇COCl, (C₂H₅)₃N
z³) 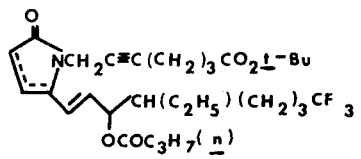
a⁴) —
a⁴) 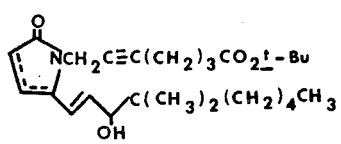
b⁴) C₂H₅I, NaH
b⁴) 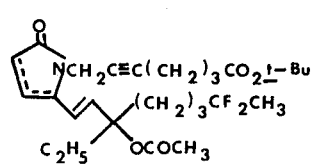
c⁴) CH₃COCl, (C₂H₅)₃N
c⁴) 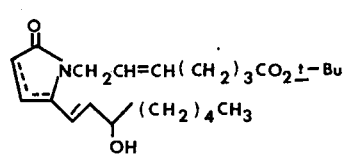
d⁴) —
d⁴)

TABLE I-continued
| | | |
|---|---|---|
| e⁴) CH₃I, NaH | e⁴) | 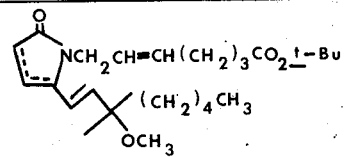 |
| f⁴) (CH₃)₂CHCOCl, (C₂H₅)₃N | f⁴) | 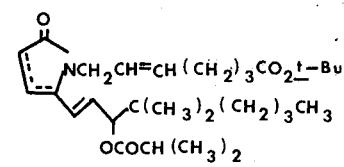 |
| g⁴) — | g⁴) | 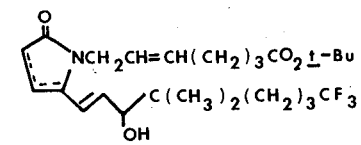 |
| h⁴) — | h⁴) | 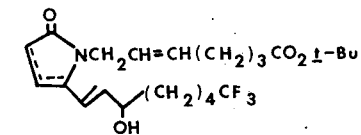 |
| i⁴) CH₃I, NaH | i⁴) | 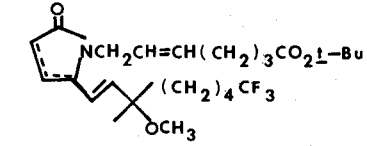 |
| j⁴) — | j⁴) | 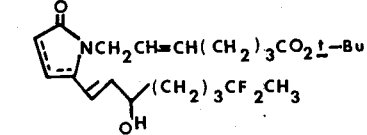 |
| k⁴) CH₃COCl, (C₂H₅)₃N | k⁴) | 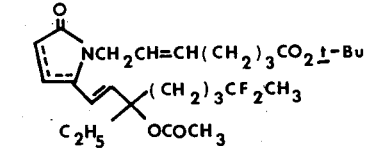 |
| l⁴) C₂H₅I, (C₂H₅)₃N | l⁴) | 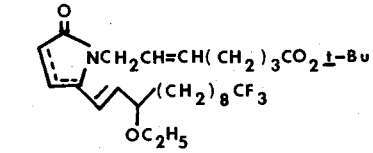 |
| m⁴) C₂H₅COCl, (C₂H₅)₃N | m⁴) | 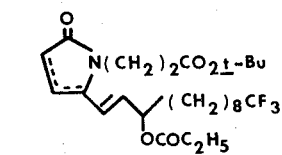 |

TABLE I-continued
n⁴) $CH_3COCl$, $(C_2H_5)_3N$   n⁴) 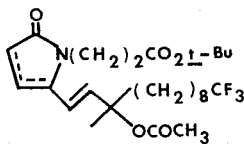
o⁴) —   o⁴) 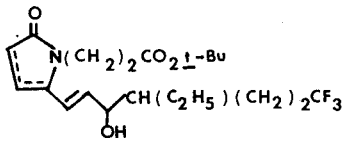
p⁴) $nC_3H_7COCl$, $(C_2H_5)_3N$   p⁴) 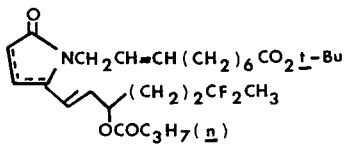
q⁴) —   q⁴) 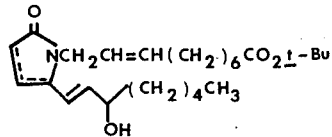
r⁴) $CH_3I$, NaH   r⁴) 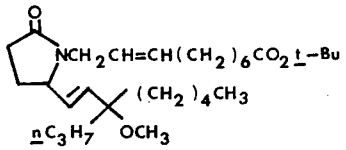
s⁴) —   s⁴) 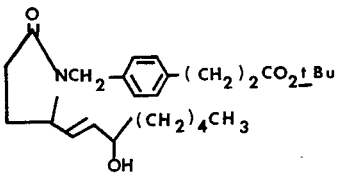
t⁴) $C_2H_5I$, NaH   t⁴) 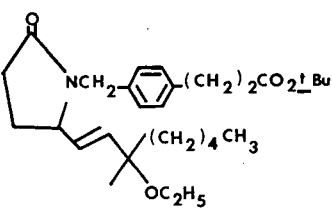
u⁴) $CH_3I$, NaH   u⁴) 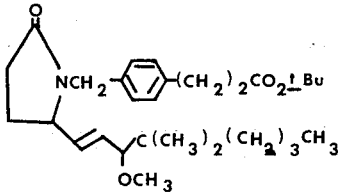

TABLE I-continued
| | | | |
|---|---|---|---|
| v⁴) | — | v⁴) | 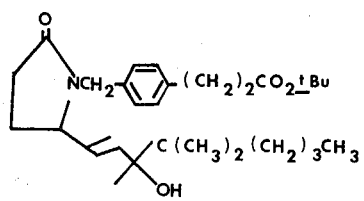 |
| w⁴) | CH₃COCl, (C₂H₅)₃N | w⁴) | 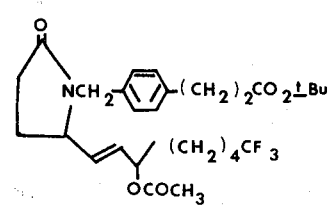 |
| x⁴) | CH₃COCl, (C₂H₅)₃N | x⁴) | 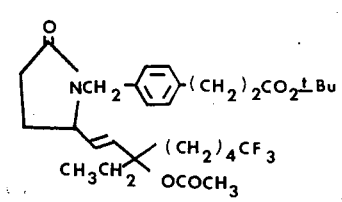 |
| y⁴) | — | y⁴) | 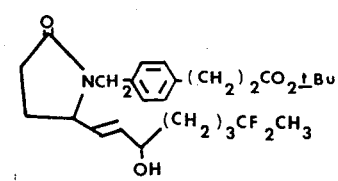 |
| z⁴) | CH₃I, NaH | z⁴) | 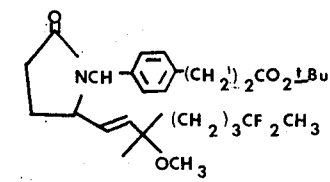 |
| a⁵) | — | a⁵) | 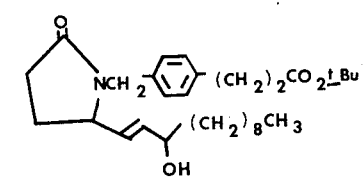 |

TABLE I-continued
| | | | |
|---|---|---|---|
| b⁵) CH₃COCl, (C₂H₅)₃N | | b⁵) | 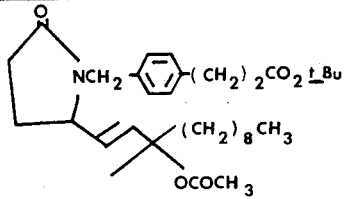 |
| c⁵) — | | c⁵) | 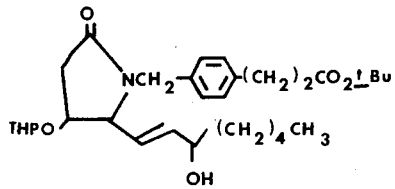 |
| d⁵) — | | d⁵) | 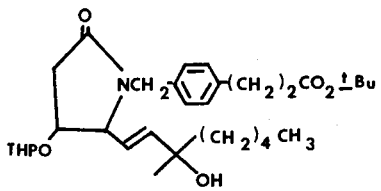 |
| e⁵) CH₃COCl, (C₂H₅)₃N | | e⁵) | 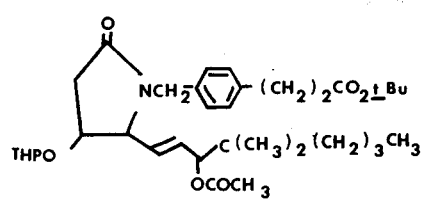 |
| f⁵) — | | f⁵) | 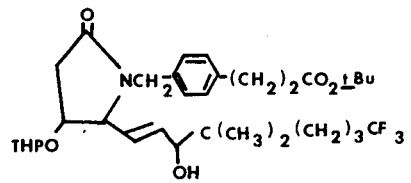 |
| g⁵) CH₃I, NaH | | g⁵) | 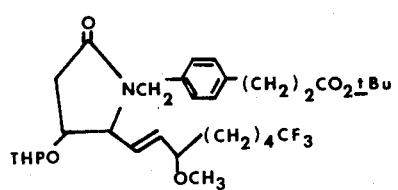 |
| h⁵) — | | h⁵) | 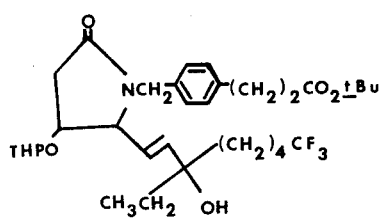 |

TABLE I-continued
i⁵) — i⁵) 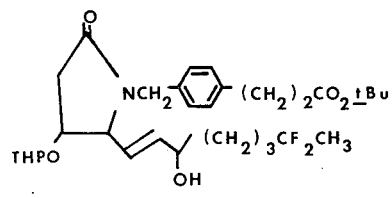
j⁵) CH₃COCl, (C₂H₅)₃N j⁵) 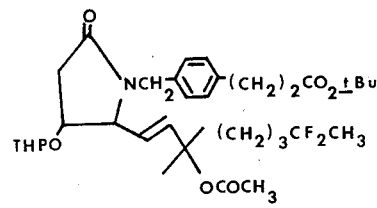
k⁵) — k⁵) 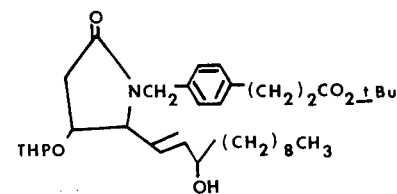
l⁵) CH₃COCl, (C₂H₅)₃N l⁵) 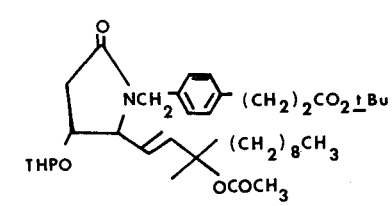
m⁵) — m⁵) 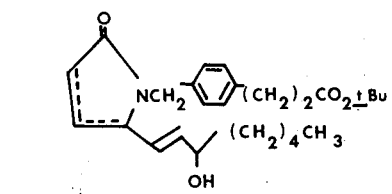
n⁵) CH₃I, NaH n⁵) 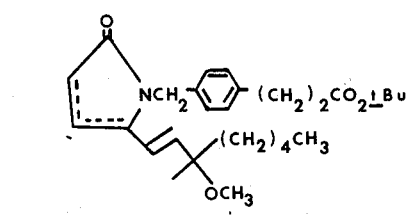
o⁵) — o⁵) 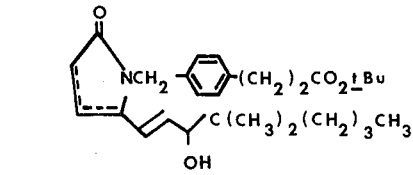

TABLE I-continued
| | | | |
|---|---|---|---|
| p⁵) C₂H₅I, NaH | | p⁵) | 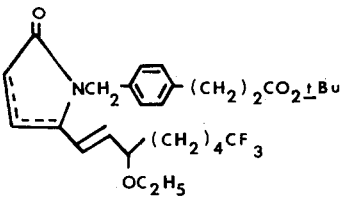 |
| q⁵) CH₃COCl, (C₂H₅)₃N | | q⁵) | 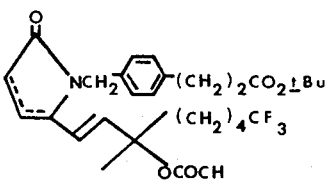 |
| r⁵) PhCH₂I, NaH | | r⁵) | 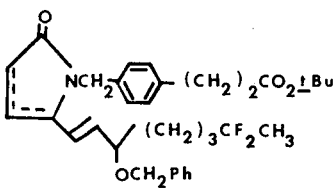 |
| s⁵) — | | s⁵) | 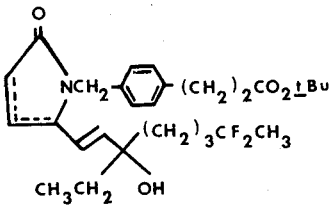 |
| t⁵) CH₃COCl, (C₂H₅)₃N | | t⁵) | 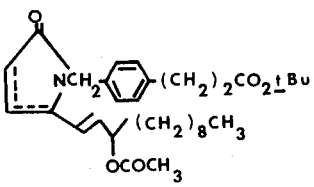 |
| K | | L | |
| a) CH₃OH | | a) | 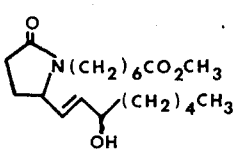 |

TABLE I-continued
| | | | |
|---|---|---|---|
| b) | — | b) | 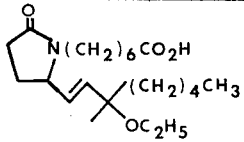 |
| c) | nC₁₀H₂₁OH | c) | 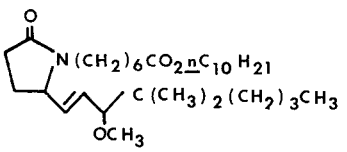 |
| d) | NaOH | d) | 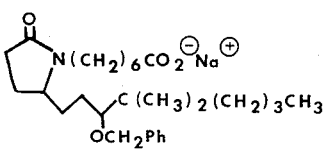 |
| e) | H₃N⁺C(CH₂OH)₃Cl⁻ | e) | 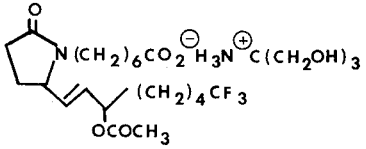 |
| f) | NaOH | f) | 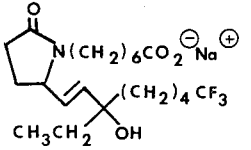 |
| g) | C₂H₅OH | g) | 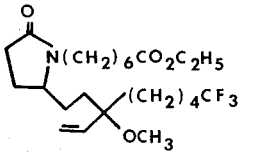 |
| h) | — | h) | 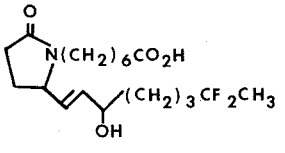 |
| i) | PhCH₂OH | i) | 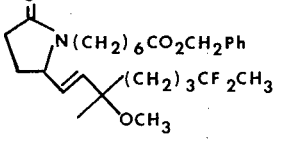 |
| j) | LiOH | j) | 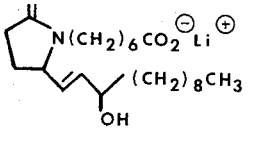 |

TABLE I-continued
k) CH₃OH    k) 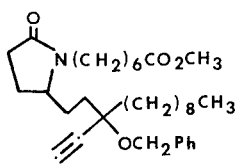
l) cC₆H₁₁OH    l) 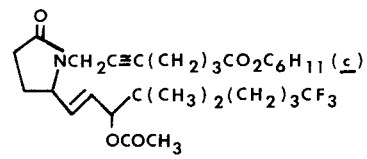
m) NaOH    m) 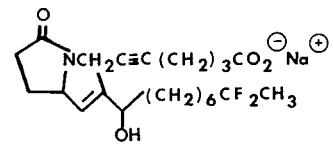
n) NaOH    n) 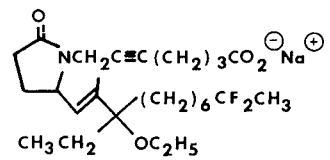
o) —    o) 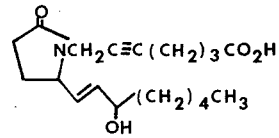
p) CH₃OH    p) 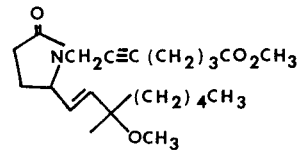
q) C₂H₅OH    q) 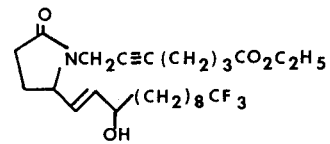
r) NaOH    r) 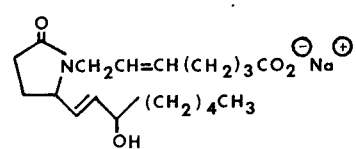

3,975,399
TABLE I-continued
| | | |
|---|---|---|
| s) $(nC_4H_9)_4N^+OH^-$ | s) | 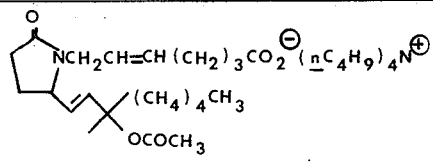 |
| t) LiOH | t) | 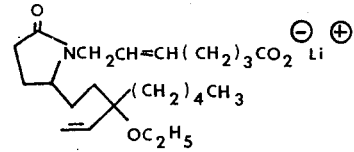 |
| u) — | u) | 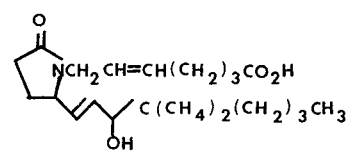 |
| v) NaOH | v) | 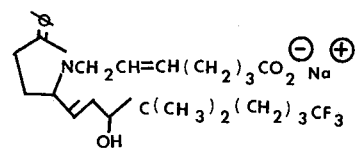 |
| w) $H_3N^+C(CH_2OH)_3^-Cl$ | w) | 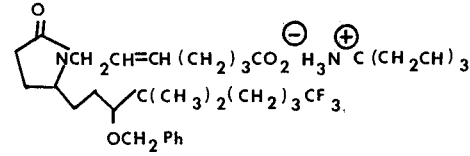 |
| x) $CH_3OH$ | x) | 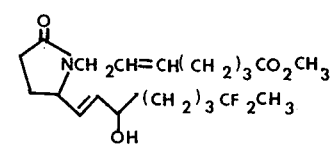 |
| y) $CH_3OH$ | y) | 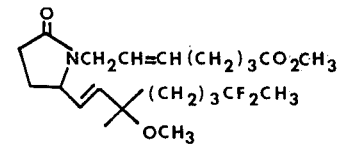 |
| z) LiOH | z) | 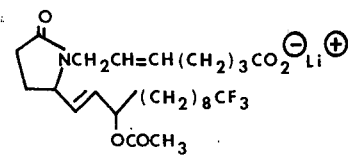 |
| $a^2$) $C_2H_5OH$ | $a^2$) | 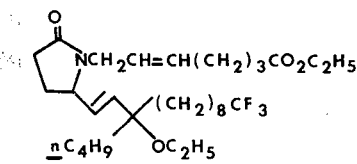 | b²) PhCH₂OH   b²) 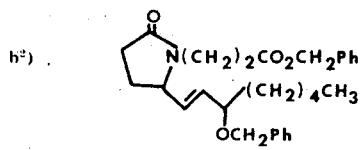
c²) (nC₄H₉)₄N⁺OH⁻   c²) 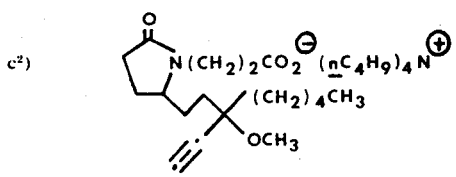
d²) NaOH   d²) 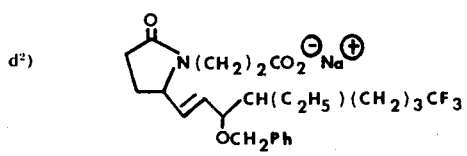
e²) —   e²) 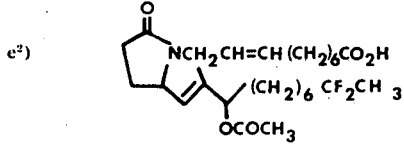
f²) —   f²) 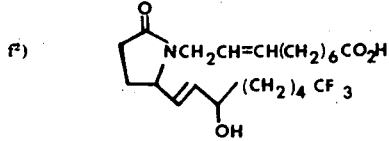
g²) C₂H₅OH   g²) 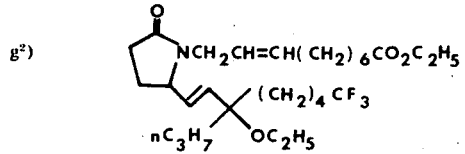
h²) —   h²) 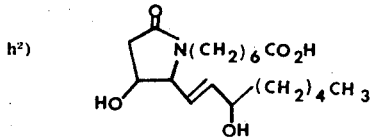
i²) CH₃OH   i²) 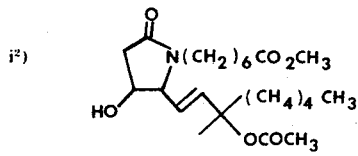

TABLE I-continued j²) NaOH     j²) pyrrolidinone with N(CH$_2$)$_6$CO$_2^\ominus$Na$^\oplus$, 4-OH, 5-CH=CH-C(CH$_3$)$_2$(CH$_2$)$_3$CH$_3$ with OH k²) cC$_6$H$_{11}$OH     k²) pyrrolidinone with N(CH$_2$)$_6$CO$_2$C$_6$H$_{11}$ (c), 4-OH, 5-CH=CH-C(CH$_3$)$_2$(CH$_2$)$_3$CF$_3$ with OCH$_3$ l²) LiOH     l²) pyrrolidinone with N(CH$_2$)$_6$CO$_2^\ominus$Li$^\oplus$, 4-OH, 5-CH=CH-CH(OH)(CH$_2$)$_4$CF$_3$ m²) C$_2$H$_5$OH     m²) pyrrolidinone with N(CH$_2$)$_6$CO$_2$C$_2$H$_5$, 4-OH, 5-CH=CH-C(CH$_3$)(OC$_2$H$_5$)(CH$_2$)$_4$CF$_3$ n²) nC$_{10}$H$_{21}$OH     n²) pyrrolidinone with N(CH$_2$)$_6$CO$_2$C$_{10}$H$_{21}$ (n), 4-OH, 5-CH=CH-C(=)(OCOCH$_3$)(CH$_2$)$_4$CF$_3$ o²) —     o²) pyrrolidinone with N(CH$_2$)$_6$CO$_2$H, 4-OH, 5-CH=CH-CH(OH)(CH$_2$)$_3$CF$_2$CH$_3$ p²) PhCH$_2$OH     p²) pyrrolidinone with N(CH$_2$)$_6$CO$_2$CH$_2$Ph, 4-OH, 5-CH=CH-C(C$_2$H$_5$)(OCH$_3$)(CH$_2$)$_3$CF$_2$CH$_3$ q²) NaOH     q²) pyrrolidinone with N(CH$_2$)$_6$CO$_2^\ominus$Na$^\oplus$, 4-OH, 5-CH=CH-CH(OCOCH$_3$)(CH$_2$)$_8$CH$_3$ r²) CH$_3$OH     r²) pyrrolidinone with NCH$_2$C≡C(CH$_2$)$_3$CO$_2$CH$_3$, 4-OH, 5-CH=CH-CH(OCH$_3$)(CH$_2$)$_4$CH$_3$ TABLE I-continued
s²) H₃N⁺C(CH₂OH)₃Cl⁻   s²) 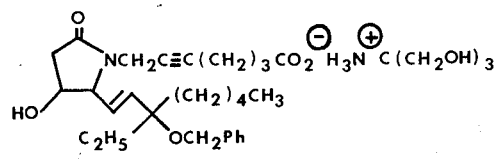
t²) —   t²) 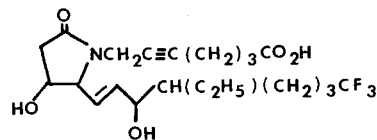
u²) LiOH   u²) 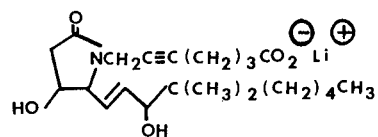
v²) C₂H₅OH   v²) 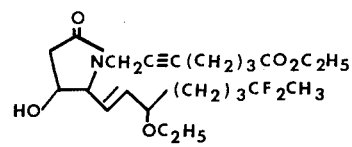
w²) nC₁₀H₂₁OH   w²) 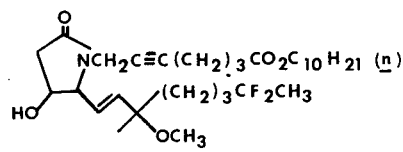
x²) —   x²) 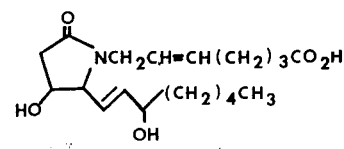
y²) NaOH   y²) 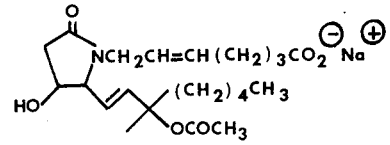
z² C₂H₅OH   z²) 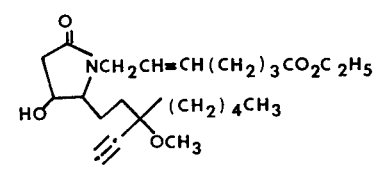

TABLE I-continued
| | | | |
|---|---|---|---|
| a³) | CH₃OH | a³) | 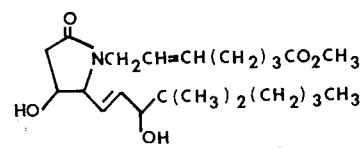 |
| b³) | — | b³) | 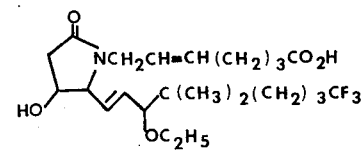 |
| c³) | LiOH | c³) | 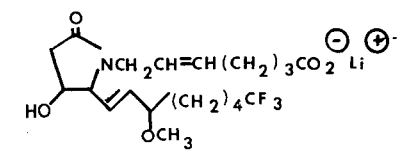 |
| d³) | c-C₅H₉OH | d³) | 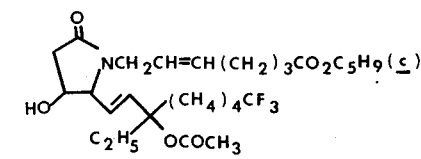 |
| e³) | — | e³) | 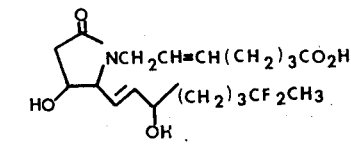 |
| f³) | LiOH | f³) | 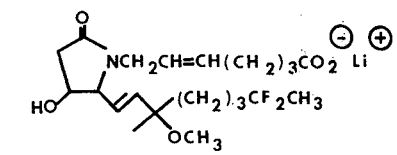 |
| g³) | (nC₄H₉)₄N⁺OH⁻ | g³) | 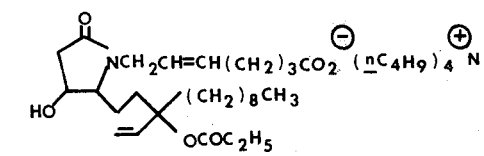 |
| h³) | H₃N⁺C(CH₂OH)₃⁻Cl | h³) | 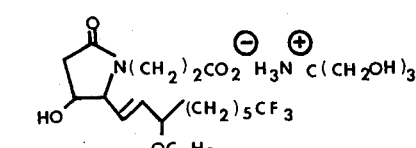 |
| i³) | PhCH₂OH | i³) | 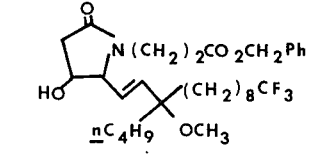 |

TABLE I-continued
j³) NaOH            j³) 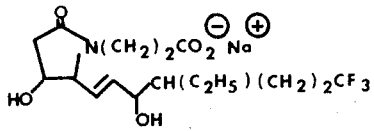
k³) —               k³) 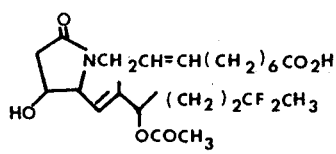
l³) (CH₃)₂CHOH      l³) 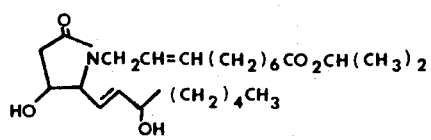
m³) CH₃OH           m³) 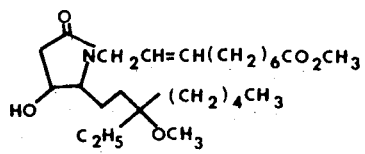
n³) —               n³) 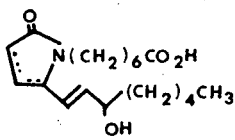
o³) —               o³) 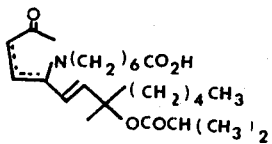
p³) nC₁₀H₂₁OH       p³) 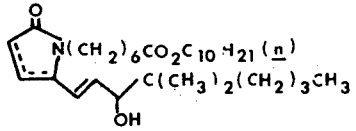
q³) LiOH            q³) 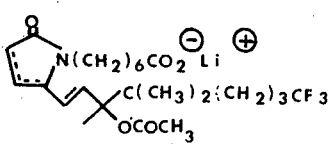

TABLE I-continued
r³) cC₆H₁₁OH  r³) 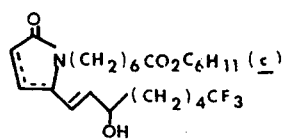
s³) NaOH  s³) 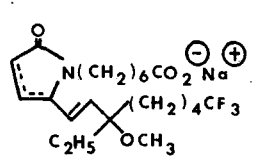
t³) (nC₄H₉)₄N⁺OH⁻  t³) 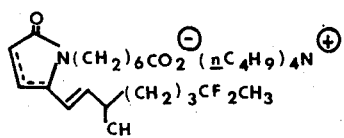
u³) —  u³) 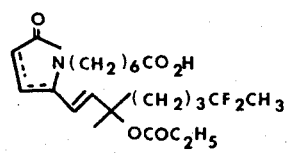
v³) NaOH  v³) 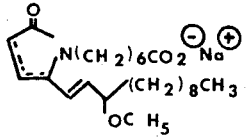
w³) LiOH  w³) 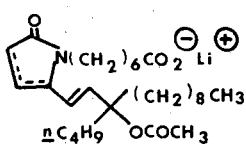
x³) —  x³) 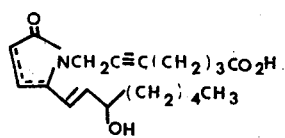
y³) CH₃OH  y³) 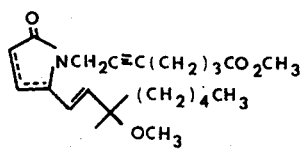

TABLE I-continued
| | | | |
|---|---|---|---|
| $z^3$) | — | $z^3$) | 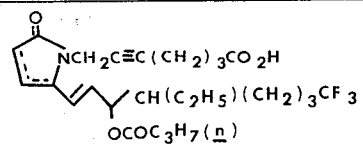 |
| $a^4$) | NaOH | $a^4$) | 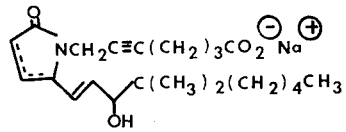 |
| $b^4$) | CH$_3$OH | $b^4$) | 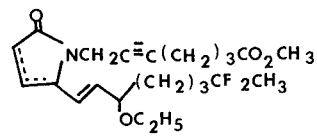 |
| $c^4$) | PhCH$_2$OH | $c^4$) | 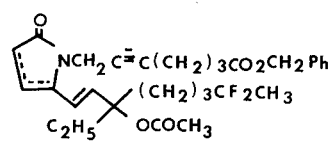 |
| $d^4$) | LiOH | $d^4$) | 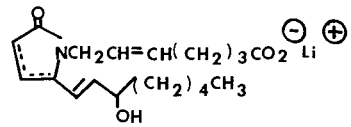 |
| $e^4$) | (CH$_3$)$_2$CHOH | $e^4$) | 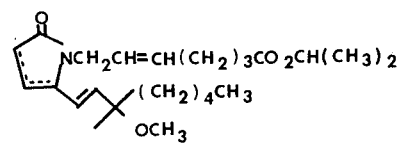 |
| $f^4$) | KOH | $f^4$) | 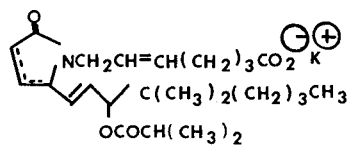 |
| $g^4$) | C$_2$H$_5$OH | $g^4$) | 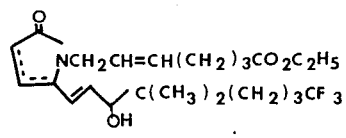 |
| $h^4$) | — | $h^4$) | 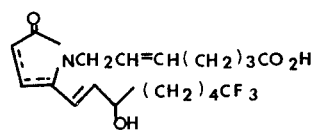 |

TABLE I-continued
i⁴) NaOH      i⁴) 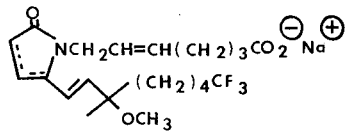
j⁴) c-C₅H₉OH      j⁴) 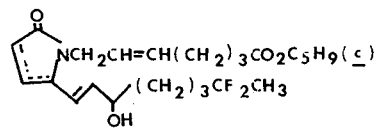
k⁴) LiOH      k⁴) 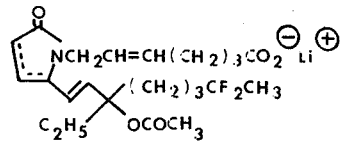
l⁴) n-C₁₀H₂₁OH      l⁴) 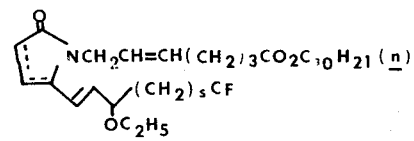
m⁴) H₃N⁺C(CH₂OH)₃Cl⁻      m⁴) 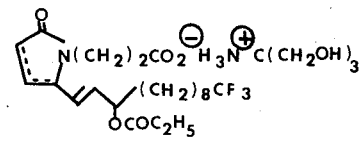
n⁴) —      n⁴) 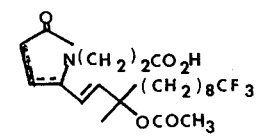
o⁴) (nC₃H₇)₄N⁺OH⁻      o⁴) 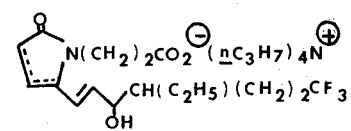
p⁴) NaOH      p⁴) 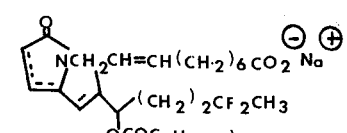

TABLE I-continued
| | | | |
|---|---|---|---|
| q⁴) LiOH | | q⁴) | 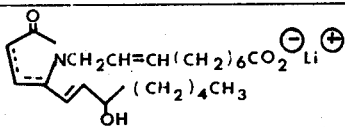 |
| r⁴) C₂H₅OH | | r⁴) | 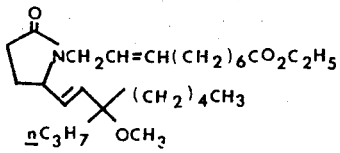 |
| s⁴) CH₃OH | | s⁴) | 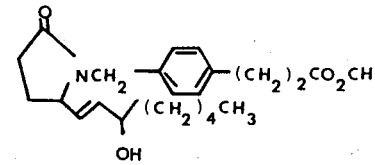 |
| t⁴) NaOH | | t⁴) | 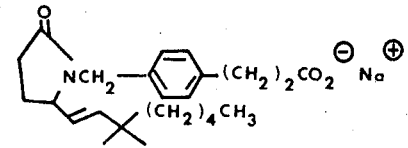 |
| u⁴) H₃N⁺C(CH₂OH)₃Cl⁻ | | u⁴) | 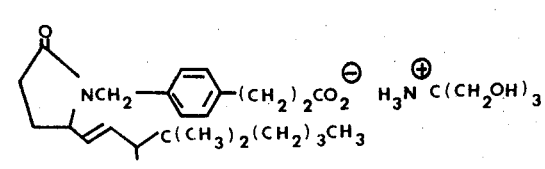 |
| v⁴) — | | v⁴) | 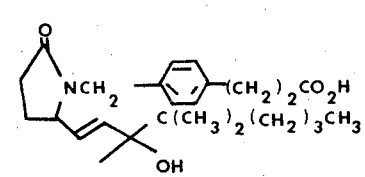 |
| w⁴) CH₃OH | | w⁴) | 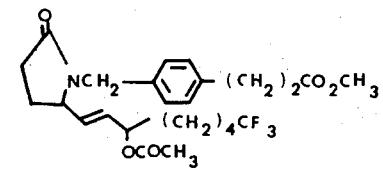 |
| x⁴) — | | x⁴) | 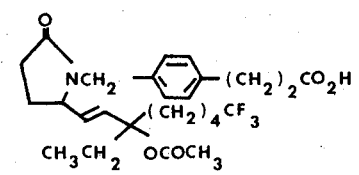 |
| y⁴) LiOH | | y⁴) | 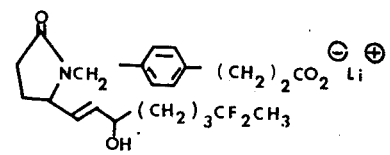 |

TABLE I-continued
| | | |
|---|---|---|
| z⁴) CH₃OH | z⁴) | 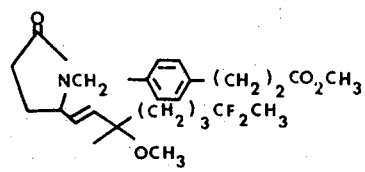 |
| a⁵) LiOH | a⁵) | 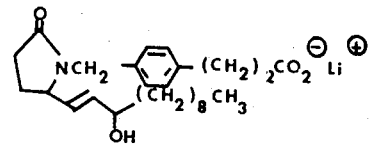 |
| b⁵) H₃N⁺C(CH₂OH)₃Cl⁻ | b⁵) | 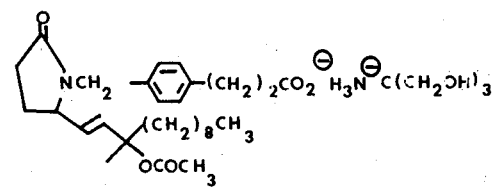 |
| c⁵) CH₃OH | c⁵) | 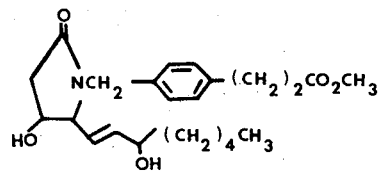 |
| d⁵) (nC₄H₉)₄N⁺OH⁻ | d⁵) | 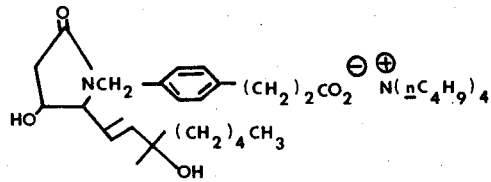 |
| e⁵) NaOH | e⁵) | 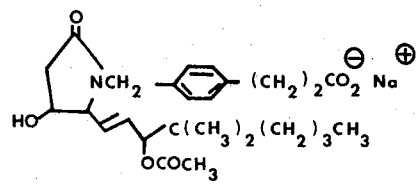 |
| f⁵) — | f⁵) | 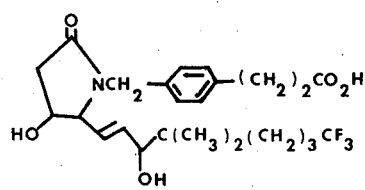 |

TABLE I-continued
| | | |
|---|---|---|
| g⁵) KOH | g⁵) | 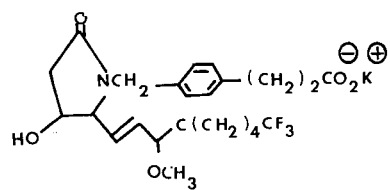 |
| h⁵) CH₃OH | h⁵) | 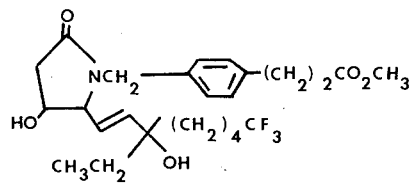 |
| i⁵) CH₃OH | i⁵) | 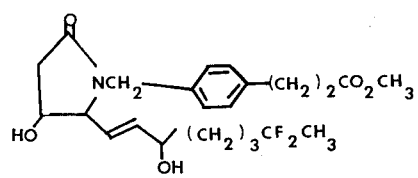 |
| j⁵) — | j⁵) | 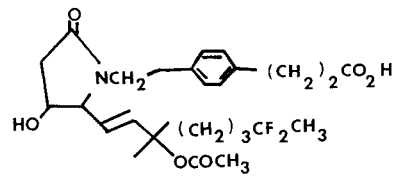 |
| k⁵) CH₃OH | k⁵) | 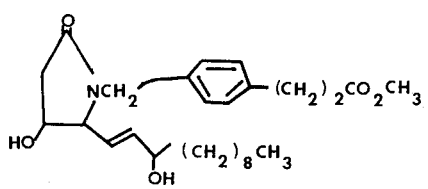 |
| l⁵) H₃N⁺C(CH₂OH)₃⁻Cl | l⁵) | 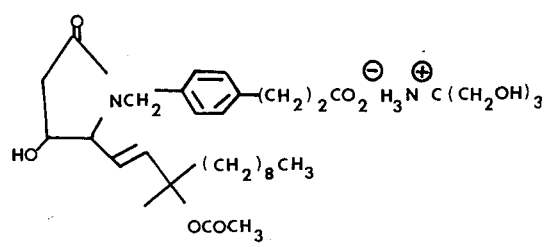 |
| m⁵) — | m⁵) | 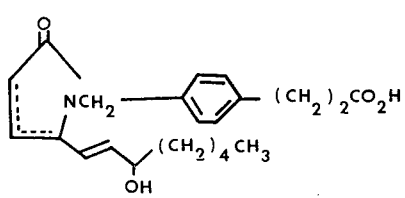 |

TABLE I-continued
n⁵) CH₃OH    n⁵) 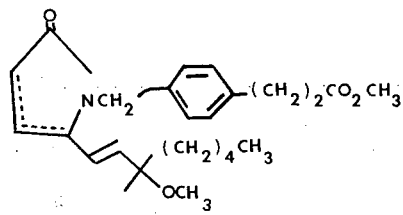
o⁵) —    o⁵) 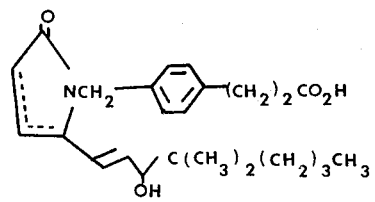
p⁵) C₂H₅OH    p⁵) 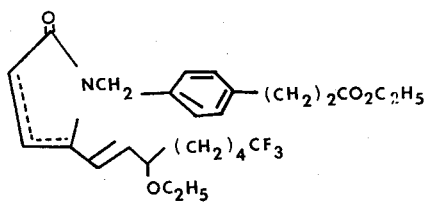
q⁵) H₃N⁺C(CH₂OH)₃Cl⁻    q⁵) 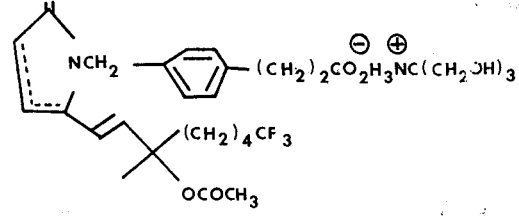
r⁵) —    r⁵) 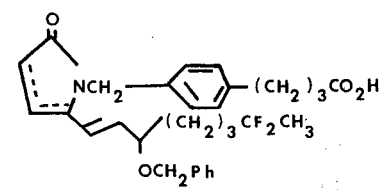
s⁵) NaOH    s⁵) 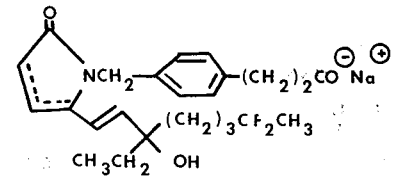

| | | | |
|---|---|---|---|
| t[5]) | — | t[5]) | 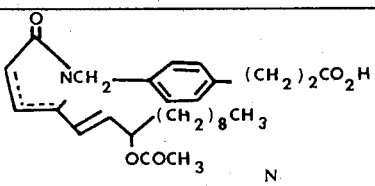 |
| | M | | N |
| h[2]) | — | h[2]) | 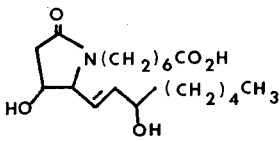 |
| i[2]) | — | i[2]) | 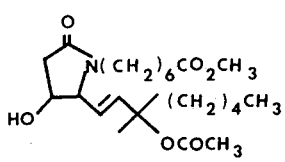 |
| j[2]) | — | j[2]) | 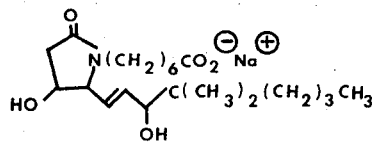 |
| k[2]) | $C_2H_5I$, NaH | k[2]) | 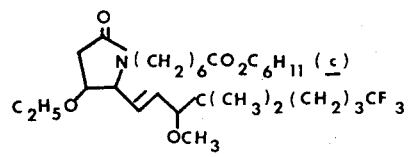 |
| l[2]) | $CH_3COCl$, $(C_2H_5)_3N$ | l[2]) | 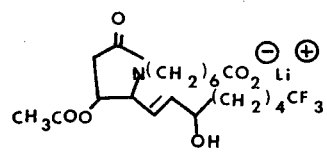 |
| m[2]) | $PhCH_2I$, NaH | m[2]) | 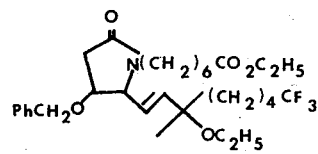 |
| n[2]) | $(CH_3)_2CHCOCl$, $(C_2H_5)_3N$ | n[2]) | 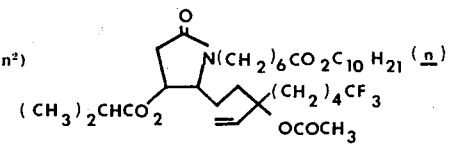 |
| o[2]) | — | o[2]) | 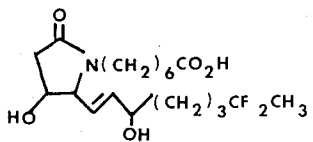 |

TABLE I-continued
p²) C₂H₅I, NaH
p²) 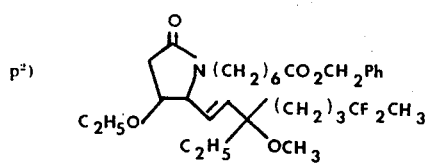
q²) —
q²) 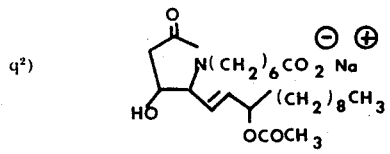
r²) CH₃COCl, (C₂H₅)₃N
r²) 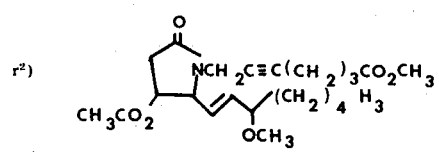
s²) —
s²) 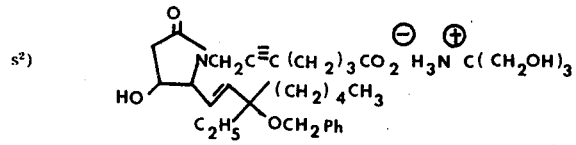
t²) —
t²) 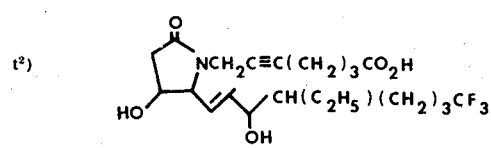
u²) —
u²) 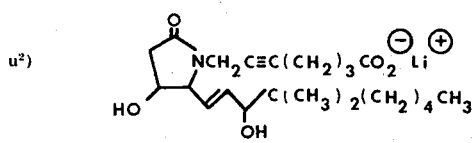
v²) nC₃H₇COCl, (C₂H₅)₃N
v²) 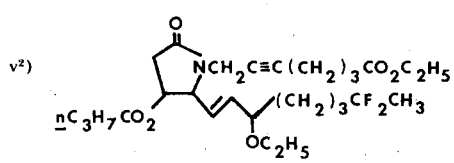
w²) —
w²) 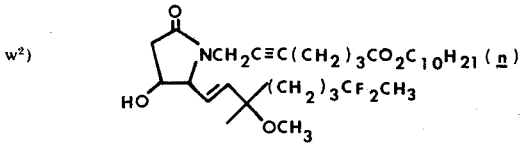

TABLE I-continued
| | | | |
|---|---|---|---|
| $x^2$ | — | $x^2$) | 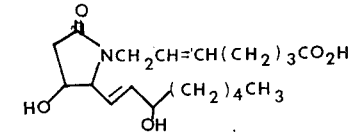 |
| $y^2$) | $C_2H_5COCl, (C_2H_5)_3N$ | $y^2$) | 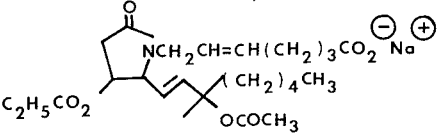 |
| $z^2$) | — | $z^2$) | 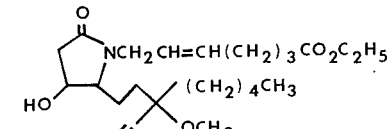 |
| $a^3$) | — | $a^3$) | 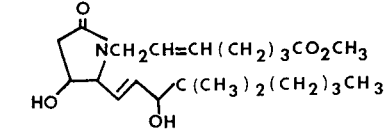 |
| $b^3$) | $CH_3COCl, (C_2H_5)_3N$ | $b^3$) | 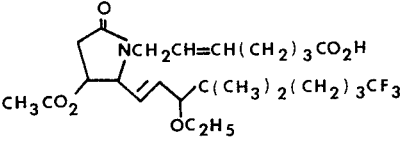 |
| $c^3$) | $CH_3COCl, (C_2H_5)_3N$ | $c^3$) | 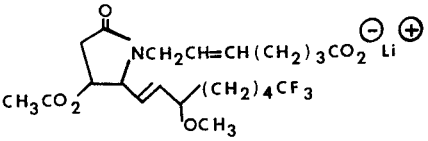 |
| $d^3$) | $CH_3I, NaH$ | $d^3$) | 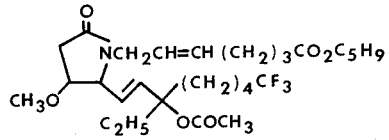 |
| $e^3$) | — | $e^3$) | 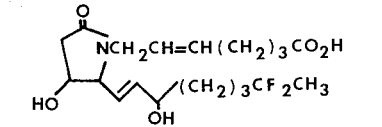 |

TABLE I-continued

| | | | |
|---|---|---|---|
| f³) | (CH₃)₂CHCOCl, (C₂H₅)₃N | f³) | [structure: pyrrolidinone with NCH₂CH=CH(CH₂)₃CO₂⁻ Li⁺; (CH₃)₂CHCO₂ substituent; (CH₂)₃CF₂CH₃ and OCH₃ side chain] |
| g³) | — | g³) | [structure: pyrrolidinone with NCH₂CH=CH(CH₂)₃CO₂⁻ (nC₄H₉)₄N⁺; HO substituent; (CH₂)₈CH₃ and OCOC₂H₅ side chain] |
| h³) | — | h³) | [structure: pyrrolidinone with N(CH₂)₂CO₂⁻ H₃N⁺C(CH₂OH)₃; HO substituent; (CH₂)₈CF₃ and OC₂H₅ side chain] |
| i³) | C₂H₅I, NaH | i³) | [structure: pyrrolidinone with N(CH₂)₂CO₂CH₂Ph; C₂H₅O substituent; (CH₂)₈CF₃, nC₄H₉, OCH₃ side chain] |
| j³) | — | j³) | [structure: pyrrolidinone with N(CH₂)₂CO₂⁻ Na⁺; HO substituent; CH(C₂H₅)(CH₂)₂CF₃ and OH side chain] |
| k³) | (CH₃)₂CHCOCl, (C₂H₅)₃N | k³) | [structure: pyrrolinone with NCH₂CH=CH(CH₂)₆CO₂H; (CH₃)₂CHCO₂ substituent; (CH₂)₂CF₂CH₃ and OCOCH₃ side chain] |
| l³) | — | l³) | [structure: pyrrolidinone with NCH₂CH=CH(CH₂)₆CO₂CH(CH₃)₂; HO substituent; (CH₂)₄CH₃ and OH side chain] |
| m³) | CH₃COCl, (C₂H₅)₃N | m³) | [structure: pyrrolidinone with NCH₂CH=CH(CH₂)₆CO₂CH₃; CH₃CO₂ substituent; (CH₂)₄CH₃, C₂H₅, OCH₃ side chain] |
| c⁵) | — | c⁵) | [structure: pyrrolidinone with NCH₂-C₆H₄-(CH₂)₂CO₂CH₃; HO substituent; (CH₂)₄CH₃ and OH side chain] |

TABLE I-continued
| | | | |
|---|---|---|---|
| d⁵) | — | d⁵) | 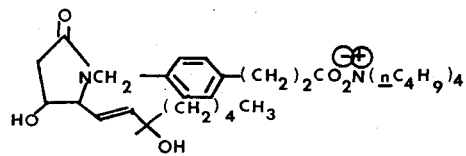 |
| e⁵) | CH₃I, NaH | e⁵) | 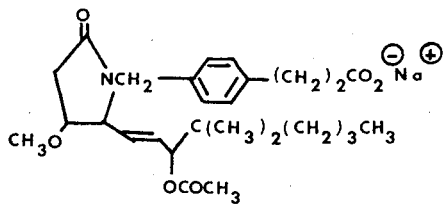 |
| f⁵) | — | f⁵) | 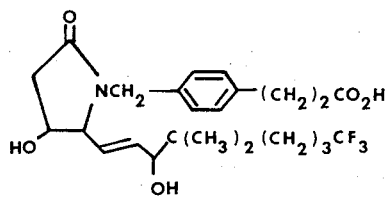 |
| g⁵) | CH₃COCl, (C₂H₅)₃N | g⁵) | 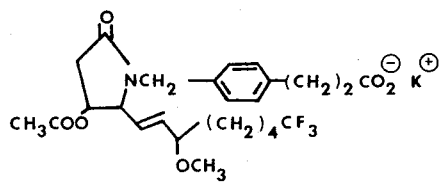 |
| h⁵) | — | h⁵) | 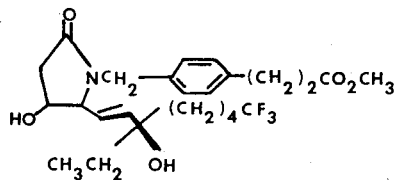 |
| i⁵) | — | i⁵) | 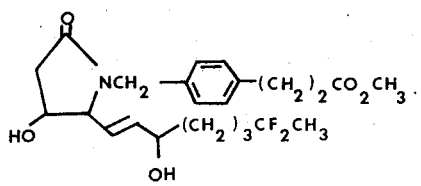 |
| j⁵) | C₂H₅I, NaH | j⁵) | 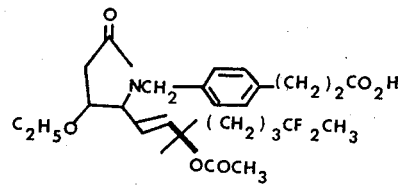 |

TABLE I-continued

| | | | |
|---|---|---|---|
| k[5]) | — | k[5]) | 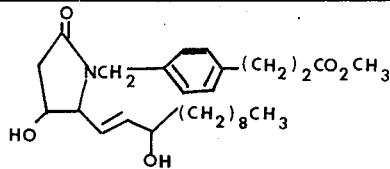 |
| l[5]) | PhCH₂l, NaH | l[5]) | 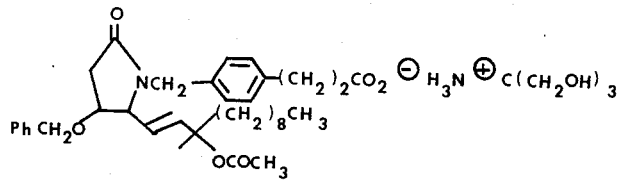 |

We claim:
1. A compound of the formula

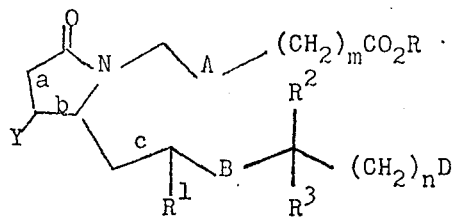

wherein

A is —CH=CH—, —C≡C—, phenylene or —CH₂—;

B is —CH₂—, <C=O or

D is —CH₃, —CF₂CH₃ or —CF₃;
Y is H or —OR[5];
R is H; alkyl of 1–10 carbons; cycloalkyl of 3–8 carbons; phenyl carbons any substituents being halogen, sulfino, sulfo, sulfamoyl, sulfanilyl, sulfoamino or sulfanilamido; aralkyl of 7–10 carbons; alkaryl of 7–10 carbons; or a physiologically acceptable cation;
R[1], R[2] and R[3] individually are H, CH₃ or C₂H₅;
R[4] is H, alkyl of 1–4 carbons, vinyl or ethynyl;
R[5] and R[6] individually are H, CH₃, C₂H₅, tetrahydropyranyl, benzyl, acyl of 1–4 carbons or trialkyl sily in which the alkyl has 1–10 carbons;
m and n individually are whole numbers in the range 1–8;
a, b and c individually are an optional additional bond with the provisos that
if c is present, only one of a and b is present; if c is absent, only one of a and b is present and A is not —C ≡ C—; if a or b is present, Y is H; and with the further provisos that
if R is tertiary butyl, Y is H,
O-tetrahydropyranyl or trialkyl silyl and R[6] is not tetrahydropyranyl.

2. A compound of claim 1 where a is present.
3. A compound of claim 1 where b is present.
4. The compound of claim 1 which is 7-[2-oxo-5-(3-oxo-1-oct-1-enyl)-1-pyrrolidinyl] heptanoic acid 5. The tertiary butyl ester of the acid of claim 4.
6. The compound of claim 1 which is 7-[2-oxo-5-(3-hydroxy-1-oct-1-enyl)-1-pyrrolidinyl] heptanoic acid.
7. The tertiary butyl ester of the acid of claim 6.
8. The compound of claim 1 which is 7-[2-oxo-5-(3-hydroxy-3-methyl-1-oct-1-enyl)-1-pyrrolidinyl] heptanoic acid.
9. The tertiary butyl ester of the acid of claim 8.
10. A compound of claim 1 where A is phenylene.
11. The compound of claim 10 which is 3-{4-[2-oxo-5-(3-hydroxy-1-oct-1-enyl)-1-pyrrolidinyl]methylphenyl}propionic acid.
12. A process comprising the steps of
A. contacting under substantially anhydrous conditions in the presence of a base and an inert solvent at a temperature range of −50° to 140°C., a lactam of the formula

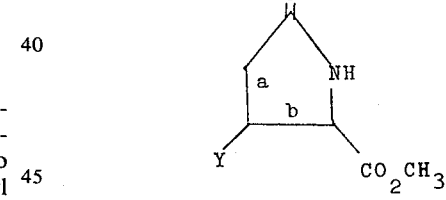

with an alkylating agent of the formula

XCH₂(A)(CH₂)ₘCO₂—C—(CH₃)₃ to obtain a product of the formula

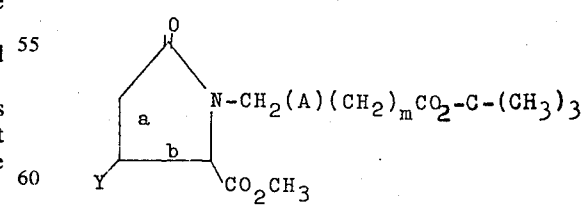

B. reacting the product of step (A) with sodium bis(2-methoxy-ethoxy)aluminum hydride under substantially anhydrous conditions in the presence of an inert solvent at a temperature range of −90° to −40°C. to obtain a product of the formula

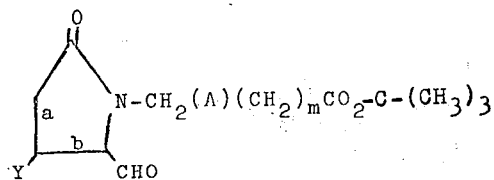

wherein
A is —$CH_2$—, —CH=CH—, —C≡C— or phenylene;
Y is H, tetrahydropyranyloxy or trialkylsilyloxy in which alkyl has 1–10 carbon atoms;

X is Br, Cl, I, tosyl, methanesulfonate, p-nitrobenzenesulfonate or trifluoroacetate;
m is a whole number from 1 to 8;
a and b individually are an additional bond with the proviso that if a or b is present Y is H.

13. The process of claim 12 in which X is Br.

14. The process of claim 12 in which the base in step (A) is nonnucleophilic with a pKb of 19 or greater.

15. The process of claim 12 in which step (A) is carried out at −50° to 120°C.

16. The process of claim 12 in which step (B) is carried out at −90° to −50°C.

* * * * *

UNITED STATES PATENT OFFICE
CERTIFICATE OF CORRECTION

PATENT NO. : 3,975,399  
DATED : August 17, 1976  
INVENTOR(S) : Robert Jay DeFranco  
Richard M. Scribner Page 1 of 2

It is certified that error appears in the above-identified patent and that said Letters Patent are hereby corrected as shown below:

Column 2, line 13, "only of" should be --only one of--.

Column 6, line 27, "mesyl chloride" should be --mesyl chloride/ --.

Column 7, line 2, "isomet" should be --isomer--.

Column 15, line 34, "or" should be --on--.

Column 16, line 36, "(a), column E" should be --(a), column F--.

Column 18, line 3, "liable" should be --labile--.

Column 24, item d), "$CF_3CH_3$" should be --$CF_2CH_3$--.

Column 37, item r)$_2$, should be
--$(CH_3O)_2P(O)CH_2COC(CH_3)_2(CH_2)_3CH_3$--.

Column 84, item g$^3$), "$(CH_2)_3CH_3$" should be --$(CH_2)_8CH_3$--

Column 106, item v), "Q" should be --O--.

Column 106, item w), "$C(CH_2CH)_3$" should be
--$C(CH_2OH)_3$--.

Column 114, item h$^3$), "$(CH_2)_5CF_3$" should be
--$(CH_2)_8CF_3$--.

UNITED STATES PATENT OFFICE
CERTIFICATE OF CORRECTION

PATENT NO. : 3,975,399
DATED : August 17, 1976
INVENTOR(S) : Robert Jay DeFranco
Richard M. Scribner It is certified that error appears in the above-identified patent and that said Letters Patent are hereby corrected as shown below:

Column 122, item $1^4$), "$(CH_2)_8CF$" should be -- $(CH_2)_8CF_3$ --.

Column 134, item $r^2$), "$(CH_2)_4H_3$" should be -- $(CH_2)_4CH_3$ --.

Column 141, line 34, "$<C=O$" should be -- $>C=O$ --.

Column 141, line 43, "phenyl carbons" should be --phenyl--.

Column 141, line 51, "sily" should be --silyl--.

Signed and Sealed this

Eleventh Day of January 1977

[SEAL]

Attest:

RUTH C. MASON
*Attesting Officer*

C. MARSHALL DANN
*Commissioner of Patents and Trademarks*